United States Patent [19]

Kay et al.

[11] Patent Number: 5,157,020
[45] Date of Patent: Oct. 20, 1992

[54] SYNTHETIC SENESCENT CELL ANTIGEN

[75] Inventors: Marguerite M. B. Kay, Temple, Tex.; John J. Marchalonis, Tucson, Ariz.

[73] Assignee: Research Corporation Tech., Inc., Tucson, Ariz.

[21] Appl. No.: 528,210

[22] Filed: May 24, 1990

[51] Int. Cl.$^5$ .................. C07K 7/08; A61K 37/02
[52] U.S. Cl. ............................ 514/13; 530/326
[58] Field of Search ................... 514/13; 530/326

[56] References Cited

FOREIGN PATENT DOCUMENTS

WO 86/05203  9/1986  PCT Int'l Appl. .

OTHER PUBLICATIONS

Kay, *Nature*, 289:491–494 (1981).
Kay et al., Mol. and Cell. Biochem., vol. 49, 1982, pp. 65–85.
Tanner et al., Biochem J., vol. 256, 1988, pp. 703–712.
Kay et al., Proc. Natl. Acad. Sci., vol. 80, pp. 1631–1635, 1983.
Kay, Proc. Natl. Acad. Sci., vol. 81, pp. 5753–5757, 1984.
Tanner, et al., *Biochem. J.*, 256:703–712 (1988).
Moriyama et al., *Arch. Biochem. and Biophys.*, 274:130–137 (1989).
Kay, *Proc. Natl. Acad. Sci. U.S.A.*, 72:3521–3525 (1975).
Kay, *J. Supramolecular Structure* 9:555–567 (1978).
Hebbel et al. *Blood*, 64:733–741 (1984).
Petz, et al. *Blood*, 64:301–304 (1984).
Kay, et al. *Proc. natl. Acad. Sci. U.S.A.*, 83:2463–2467 (1986).
Kay, et al. *Proc. Natl. Acad. Sci. U.S.A.*, 86:5834–5838 (1989).

*Primary Examiner*—Lester L. Lee
*Assistant Examiner*—Avis Davenport
*Attorney, Agent, or Firm*—Dickstein, Shapiro & Morin

[57] ABSTRACT

Disclosed herein is a synthetic senescent cell antigen comprised of purified peptides immunoreactive with antibodies to the naturally occurring antigen. Preferably, the synthetic senescent cell antigen comprises two peptides with the amino acid sequences SKLIKIFQDHPLQKTYN and LFKPPKYHPDVPYVKR, respectively. The antigen and peptides may be used in compositions, diagnostic kits, and methods for detecting or measuring antibodies to senescent cell antigen, studying cellular aging and autoimmune mechanisms, separating anions from a gas or liquid, or treating certain diseases.

37 Claims, 12 Drawing Sheets

```
                                    GGAACGAGTGGGAACGTAGCTGGTCGCAGA  -121
GGGCACCAGCGGCTGCAGGACTTCACCAAGGGACCCTGAGGCTCGTGAGCAGGGACCCGC
GGTGCGGGTTATGCTGGGGGCTCAGATCACCGTAGACAACTGGACACTCAGGACCACGCC    -1
              10                                     20
      M  E  E  L  Q  D  D  Y  E  D  M  M  E  E  N  L  E  Q  E  E
      ATGGAGGAGCTGCAGGATGATTATGAAGACATGATGGAGGAGAATCTGGAGCAGGAGGAA
              30                                     40
       Y  E  D  P  D  I  P  E  S  Q  M  E  E  P  A  A  H  D  T  E
      TATGAAGACCCAGACATCCCCGAGTCCCAGATGGAGGAGCCGGCAGCTCACGACACCGAG    120
              50                                     60
       A  T  A  T  D  Y  H  T  T  S  H  P  G  T  H  E  V  Y  V  E
      GCAACAGCCACAGACTACCACACCACATCACACCCGGGTACCCACGAGGTCTATGTGGAG
              70                                     80
       L  Q  E  L  V  M  D  E  K  N  Q  E  L  R  W  M  E  A  A  R
      CTGCAGGAGCTGGTGATGGACGAAAAGAACCAGGAGCTGAGATGGATGGAGGCGGCGCGC   240
              90                                    100
       W  V  Q  L  E  E  N  L  G  E  N  G  A  W  G  R  P  H  L  S
      TGGGTGCAACTGGAGGAGAACCTGGGGGAGAATGGGGCCTGGGGCCGCCCGCACCTCTCT
             110                                    120
       H  L  T  F  W  S  L  L  E  L  R  R  V  F  T  K  G  T  V  L
      CACCTCACCTTCTGGAGCCTCCTAGAGCTGCGTAGAGTCTTCACCAAGGGTACTGTCCTC   360
             130                                    140
       L  D  L  Q  E  T  S  L  A  G  V  A  N  Q  L  L  D  R  F  I
      CTAGACCTGCAAGAGACCTCCCTGGCTGGAGTGGCCAACCAACTGCTAGACAGGTTTATC
             150                                    160
       F  E  D  Q  I  R  P  Q  D  R  E  E  L  L  R  A  L  L  L  K
      TTTGAAGACCAGATCCGGCCTCAGGACCGAGAGGAGCTGCTCCGGGCCCTGCTGCTTAAA   480
             170                                    180
       H  S  H  A  G  E  L  E  A  L  G  G  V  K  P  A  V  L  T  R
      CACAGCCACGCTGGAGAGCTGGAGGCCCTGGGGGGTGTGAAGCCTGCAGTCCTGACACGC
             190                                    200
       S  G  D  P  S  Q  P  L  L  P  Q  H  S  S  L  E  T  Q  L  F
      TCTGGGGATCCTTCACAGCCTCTGCTCCCCCAACACTCCTCACTGGAGACACAGCTCTTC   600
             210                                    220
       C  E  Q  G  D  G  G  T  E  G  H  S  P  S  G  I  L  E  K  I
      TGTGAGCAGGGAGATGGGGGCACAGAAGGGCACTCACCATCTGGAATTCTGGAAAAGATT
             230                                    240
       P  P  D  S  E  A  T  L  V  L  V  G  R  A  D  F  L  E  Q  P
      CCCCCGGATTCAGAGGCCACGTTGGTGCTAGTGGGCCGCGCCGACTTCCTGGAGCAGCCG    720
```

FIG.1A

```
                                    250                              260
        V  L  G  F  V  R  L  Q  E  A  A  E  L  E  A  V  E  L  P  V
        GTGCTGGGCTTCGTGAGGCTGCAGGAGGCAGCGGAGCTGGAGGCGGTGGAGCTGCCGGTG
                                    270                              280
        P  I  R  F  L  F  V  L  L  G  P  E  A  P  H  I  D  Y  T  Q
        CCTATACGCTTCCTCTTTGTGTTGCTGGGACCTGAGGCCCCCCACATCGATTACACCCAG    840
                                    290                              300
        L  G  R  A  A  A  T  L  M  S  E  R  V  F  R  I  D  A  Y  M
        CTTGGCCGGGCTGCTGCCACCCTCATGTCAGAGAGGGTGTTCCGCATAGATGCCTACATG
                                    310                              320
        A  Q  S  R  G  E  L  L  H  S  L  E  G  F  L  D  C  S  L  V
        GCTCAGAGCCGAGGGGAGCTGCTGCACTCCCTAGAGGGCTTCCTGGACTGCAGCCTAGTG    960
                                    330                              340
        L  P  P  T  D  A  P  S  E  Q  A  L  L  S  L  V  P  V  Q  R
        CTGCCTCCCACCGATGCCCCCTCCGAGCAGGCACTGCTCAGTCTGGTGCCTGTGCAGAGG
                                    350                              360
        E  L  L  R  R  R  Y  Q  S  S  P  A  K  P  D  S  S  F  Y  K
        GAGCTACTTCGAAGGCGCTATCAGTCCAGCCCTGCCAAGCCAGACTCCAGCTTCTACAAG    1080
                                    370                              380
        G  L  D  L  N  G  G  P  D  D  P  L  Q  Q  T  G  Q  L  F  G
        GGCCTAGACTTAAATGGGGGCCCAGATGACCCTCTGCAGCAGACAGGCCAGCTCTTCGGG
                                    390                              400
        G  L  V  R  D  I  R  R  R  Y  P  Y  Y  L  S  D  I  T  D  A
        GGCCTGGTGCGTGATATCCGGCGCCGCTACCCCTATTACCTGAGTGACATCACAGATGCA    1200
                                    410                              420
        F  S  P  Q  V  L  A  A  V  I  F  I  Y  F  A  A  L  S  P  A
        TTCAGCCCCCAGGTCCTGGCTGCCGTCATCTTCATCTACTTTGCTGCACTGTCACCCGCC
                                    430                              440
        I  T  F  G  G  L  L  G  E  K  T  R  N  Q  M  G  V  S  E  L
        ATCACCTTCGGCGGCCTCCTGGGAGAAAAGACCCGGAACCAGATGGGAGTGTCGGAGCTG    1320
                                    450                              460
        L  I  S  T  A  V  Q  G  I  L  F  A  L  L  G  A  Q  P  L  L
        CTGATCTCCACTGCAGTGCAGGGCATTCTCTTCGCCCTGCTGGGGGCTCAGCCCCTGCTT
                                    470                              480
        V  V  G  F  S  G  P  L  L  V  F  E  E  A  F  F  S  F  C  E
        GTGGTCGGCTTCTCAGGACCCCTGCTGGTGTTTGAGGAAGCCTTCTTCTCGTTCTGCGAG    1440
                                    490                              500
        T  N  G  L  E  Y  I  V  G  R  V  W  I  G  F  W  L  I  L  L
        ACCAACGGTCTAGAGTACATCGTGGGCCGCGTGTGGATCGGCTTCTGGCTCATCCTGCTG
                                    510                              520
        V  V  L  V  V  A  F  E  G  S  F  L  V  R  F  I  S  R  Y  T
        GTGGTGTTGGTGGTGGCCTTCGAGGGTAGCTTCCTGGTCCGCTTCATCTCCCGCTATACC    1560
```

FIG.1B

```
                        530                             540
      Q  E  I  F  S  F  L  I  S  L  I  F  I  Y  E  T  F  S  K  L
      CAGGAGATCTTCTCCTTCCTCATTTCCCTCATCTTCATCTATGAGACTTTCTCCAAGCTG
                        550                             560
      I  K  I  F  Q  D  H  P  L  Q  K  T  Y  N  Y  N  V  L  M  V
      ATCAAGATCTTCCAGGACCACCCACTACAGAAGACTTATAACTACAACGTGTTGATGGTG      1680
                        570                             580
      P  K  P  Q  G  P  L  P  N  T  A  L  L  S  L  V  L  M  A  G
      CCCAAACCTCAGGGCCCCCTGCCCAACACAGCCCTCCTCTCCCTTGTGCTCATGGCCGGT
                        590                             600
      T  F  F  F  A  M  M  L  R  K  F  K  N  S  S  Y  F  P  G  K
      ACCTTCTTCTTTGCCATGATGCTGCGCAAGTTCAAGAACAGCTCCTATTTCCCTGGCAAG      1800
                        610                             620
      L  R  R  V  I  G  D  F  G  V  P  I  S  I  L  I  M  V  L  V
      CTGCGTCGGGTCATCGGGGACTTCGGGGTCCCCATCTCCATCCTGATCATGGTCCTGGTG
                        630                             640
      D  F  F  I  Q  D  T  Y  T  Q  K  L  S  V  P  D  G  F  K  V
      GATTTCTTCATTCAGGATACCTACACCCAGAAACTCTCGGTGCCTGATGGCTTCAAGGTG      1920
                        650                             660
      S  N  S  S  A  R  G  W  V  I  H  P  L  G  L  R  S  E  F  P
      TCCAACTCCTCAGCCCGGGGCTGGGTCATCCACCCACTGGGCTTGCGTTCCGAGTTTCCC
                        670                             680
      I  W  M  M  F  A  S  A  L  P  A  L  L  V  F  I  L  I  F  L
      ATCTGGATGATGTTTGCCTCCGCCCTGCCTGCTCTGCTGGTCTTCATCCTCATATTCCTG      2040
                        690                             700
      E  S  Q  I  T  T  L  I  V  S  K  P  E  R  K  M  V  K  G  S
      GAGTCTCAGATCACCACGCTGATTGTCAGCAAACCTGAGCGCAAGATGGTCAAGGGCTCC
                        710                             720
      G  F  H  L  D  L  L  L  V  V  G  M  G  G  V  A  A  L  F  G
      GGCTTCCACCTGGACCTGCTGCTGGTAGTAGGCATGGGTGGGGTGGCCGCCCTCTTTGGG      2160
                        730                             740
      M  P  W  L  S  A  T  T  V  R  S  V  T  H  A  N  A  L  T  V
      ATGCCCTGGCTCAGTGCCACCACCGTGCGTTCCGTCACCCATGCCAACGCCCTCACTGTC
                        750                             760
      M  G  K  A  S  T  P  G  A  A  A  Q  I  Q  E  V  K  E  Q  R
      ATGGGCAAAGCCAGCACCCCAGGGGCTGCAGCCCAGATCCAGGAGGTCAAAGAGCAGCGG      2280
```

FIG.1C

```
                       770                              780
  I  S  G  L  L  V  A  V  L  V  G  L  S  I  L  M  E  P  I  L
ATCAGTGGACTCCTGGTCGCTGTGCTTGTGGGCCTGTCCATCCTCATGGAGCCCATCCTG
                       790                              800
  S  R  I  P  L  A  V  L  F  G  I  F  L  Y  M  G  V  T  S  L
TCCCGCATCCCCCTGGCTGTACTGTTTGGCATCTTCCTCTACATGGGGGTCACGTCGCTC   2400
                       810                              820
  S  G  I  Q  L  F  D  R  I  L  L  L  F  K  P  P  K  Y  H  P
AGCGGCATCCAGCTCTTTGACCGCATCTTGCTTCTGTTCAAGCCACCCAAGTATCACCCA
                       830                              840
  D  V  P  Y  V  K  R  V  K  T  W  R  M  H  L  F  T  G  I  Q
GATGTGCCCTACGTCAAGCGGGTGAAGACCTGGCGCATGCACTTATTCACGGGCATCCAG   2520
                       850                              860
  I  I  C  L  A  V  L  W  V  V  K  S  T  P  A  S  L  A  L  P
ATCATCTGCCTGGCAGTGCTGTGGGTGGTGAAGTCCACGCCGGCCTCCCTGGCCCTGCCC
                       870                              880
  F  V  L  I  L  T  V  P  L  R  R  V  L  L  P  L  I  F  R  N
TTCGTCCTCATCCTCACTGTGCCGCTGCGGCGCGTCCTGCTGCCGCTCATCTTCAGGAAC   2640
                       890                              900
  V  E  L  Q  C  L  D  A  D  D  A  K  A  T  F  D  E  E  E  G
GTGGAGCTTCAGTGTCTGGATGCTGATGATGCCAAGGCAACCTTTGATGAGGAGGAAGGT
                       910
  R  D  E  Y  D  E  V  A  M  P  V  *
CGGGATGAATACGACGAAGTGGCCATGCCTGTGTGAGGGGCGGGCCCAGGCCCTAGACCC   2760
TCCCCCACCATTCCACATCCCCACCTTCCAAGGAAAAGCAGAAGTTCATGGGCACCTCAT
GGACTCCAGGATCCTCCTGGAGCAGCAGCTGAGGCCCCAGGGCTGTGGGTGGGGAAGGAA   2880
GGCGTGTCCAGGAGACCTTCCACAAAGGGTAGCCTGGCTTTTCTGGCTGGGGATGGCCGA
TGGGGCCCACATTAGGGGGTTTGTTGCACAGTCCCTCCTGTTGCCACACTTTCACTGGGG   3000
ATCCCGTGCTGGAAGACTTAGATCTGAGCCCTCCCTCTTCCCAGCACAGGCAGGGGTAGA
AGCAAAGGCAGGAGGTGGGTGAGCGGGTGGGGTGCTTGCTGTGTGACCTTGGGCAAGTCC   3120
CTTGACCTTTCCAGCCTATATTTCCTCTTCTGTAAAATGGGTATATTGATGATAATACCC
ACATTACAGGATGGTTACTGAGGACCAAAGATACATGTAAAATAGGGCTTTGTAAACTCC   3240
ACAGGGACTGTTCTATAGCAGTCATCATTTGTCTTTGAACGTACCCAAGGTCACATAGCT
GGGATTTGAACTGAGCCGTGCAGCT    3325
```

SYNTHETIC SENESCENT CELL ANTIGEN

FIELD OF THE INVENTION

This invention relates to a synthetic senescent cell antigen comprised of purified peptides immunoreactive with antibodies to the naturally occurring antigen. The antigen and peptides may be used in compositions, diagnostic kits, and methods for detecting or measuring antibodies to senescent cell antigen, studying cellular aging and autoimmune mechanisms, separating anions from a gas or liquid, or treating certain diseases. Thus, the invention is expected to have a wide variety of scientific, diagnostic, and clinical applications.

REFERENCES

Several publications are referenced herein by Arabic numerals within parenthesis. Full citations for these references may be found at the end of the specification immediately preceding the claims. The disclosures of these publications are hereby incorporated herein by reference in their entirety, unless otherwise noted.

BACKGROUND OF THE INVENTION

Senescent cell antigen (SCA), an aging antigen, is a protein that appears on old cells and acts as a specific signal for the termination of that cell by initiating the binding of IgG autoantibody and subsequent removal by phagocytes (1-14). This appears to be a general physiologic process for removing senescent and damaged cells in mammals and other vertebrates (4). Although the initial studies were done using human erythrocytes as a model, senescent cell antigen occurs on all cells examined (4). Besides its role in the removal of senescent and damaged cells, senescent cell antigen also appears to be involved in the removal of erythrocytes in clinical hemolytic anemias (7) and sickle cell anemia (8). It also appears to be involved in the removal of malaria-infected erythrocytes (15). Oxidation generates senescent cell antigen in situ (6).

Senescent cell antigen has been isolated from sialoglycoprotein mixtures with affinity columns prepared with IgG eluted from senescent cells (4). Both glycoprotein and protein stains of gels of the eluted material revealed a band migrating at a relative molecular weight of 62,000 in the component 4.5 region. These experiments suggested that the 62,000 $M_r$ glycoprotein carried the antigenic determinants recognized by IgG obtained from freshly isolated senescent cells. The 62,000 $M_r$ protein, but not the remaining sialoglycoprotein mixture from which it was isolated, abolished the phagocytosis-inducing ability of IgG eluted from senescent RBC in the erythrophagocytosis assay. This indicated that the 62,000 $M_r$ protein is the antigen which appeared on the membrane of the cells as they aged.

The aging antigen is derived from protein band 3, an important structural and membrane transport molecule (5). Band 3, is a ubiquitous protein (16-20). It has been found in diverse cell types and tissues besides erythrocytes, including hepatocytes (16), squamous epithelial cells (16), alveolar (lung) cells (16), lymphocytes (16), kidney (21), neurons (16, 17), and fibroblasts (16, 20). Band 3 is also present in nuclear (16), golgi (18), and mitochondrial membranes (19) as well as in cell membranes. Band 3-like proteins in nucleated cells participate in band 3 antibody induced cell surface patching and capping (16). Band 3 maintains acid-base balance by mediating the exchange of anions (e.g. chloride, bicarbonate) (22-24). Because of its central role in respiration of $CO_2$, band 3 is the most heavily used ion transport system in vertebrate animals. Band 3 is a major transmembrane structural protein (25) which attaches the plasma membrane to the internal cell cytoskeleton by binding to band 2.1 (ankyrin) (26). The transport and the cytoskeletal domains can be separated by proteolysis with trypsin. Digestion with trypsin yields a 52,000 Da membrane bound transport domain and a 40,000 Da water-soluble cytoplasmic domain that binds cytoskeletal proteins. The transport domain of band 3 is highly conserved evolutionarily and no polymorphisms of it have been found. Senescent cell antigen (SCA) is generated on this transport domain (5).

Tanner et al. (*Biochem. J.* 256:703-712 (1988), incorporated herein by reference) isolated cDNA clones corresponding to the band 3 protein for human red blood cells and determined the deduced amino acid sequence. The paper discusses certain internal and external regions of the protein.

The inventors have determined the location and sequence of two peptide fragments corresponding to separate portions of the band 3 protein, each of which is immunoreactive with the IgG autoantibody and partially blocks the binding of such antibody to naturally occurring SCA. The inventors have also surprisingly discovered that the separate peptide fragments act together synergistically to substantially block the binding of the autoantibody to naturally occurring SCA and, therefore, together comprise a synthetic senescent cell antigen. The synthetic SCA and peptide components are expected to have a wide variety of scientific, diagnostic, and clinical applications.

SUMMARY OF THE INVENTION

It is an object of the present invention to provide purified peptides immunoreactive with antibodies to SCA.

It is a further object of the invention to provide a synthetic SCA comprising mixtures of such peptides or comprising a composition where such peptides have been covalently linked.

Another object of the invention is to provide a method and kit for detecting or measuring the presence of antibodies to SCA in a sample.

Yet another object of the invention is to provide a method of inhibiting the binding of senescent cell IgG to senescent cells.

Still another object of the invention is to provide a method and apparatus for separating or trapping anions from a gas or a liquid.

A further object of the invention is to provide pharmaceutical or cosmetic compositions containing the synthetic antigen and peptides of the invention.

A still further object of the invention is to provide methods for influencing cellular aging, treating autoimmune disease, or increasing the immune response in an animal.

Additional objects and advantages of the invention will be set forth in part in the description which follows, and in part will be obvious from the description, or may be learned by the practice of the invention. The objects and advantages of the invention will be attained by means of the instrumentalities and combinations particularly pointed out in the appended claims.

To achieve the objects and in accordance with the purpose of the invention, as embodied and broadly described herein, the present invention provides a synthetic SCA. In one embodiment, the synthetic SCA comprises a mixture of peptides immunoreactive with antibodies to SCA. In an alternative embodiment, the immunoreactive peptides are chemically linked. Preferably, the synthetic SCA comprises two peptides with the amino acid sequences SKLIKIFQDHPLQKTYN and LFKPPKYHPDVPYVKR, respectively.

In another embodiment, the invention comprises a method and kit for detecting or measuring antibodies to SCA in a sample. The method comprises: (1) contacting a sample suspected of containing the antibodies with the synthetic SCA or a component peptide of the invention for a period of time and under conditions sufficient for an immunological reaction to occur between the antigen or peptide and the antibodies; and (2) determining if the reaction has occurred. The kit comprises a container containing the synthetic SCA or peptide and a means for detecting or measuring the immunological reaction. Preferably, the latter comprises a detectably labeled anti-antibody to such antibodies or a detectably labeled antibody to the synthetic SCA or peptide.

The invention further provides a method of inhibiting the binding of senescent cell IgG to senescent cells in vitro or in vivo by administering a sufficient amount of the synthetic SCA or a component peptide to inhibit such binding in such in vitro or in vivo system.

The invention also provides a method and apparatus for separating or trapping anions from a gas or a liquid. A sufficient amount of the synthetic SCA or one of the component peptides is contacted with the gas or liquid for a sufficient amount of time to form complexes between the antigen or peptide and the anions. The complexes are then separated from the gas or liquid. Preferably, the synthetic antigen or peptide is bound to an insoluble matrix in an affinity column. In an alternative preferred embodiment, it is bound to a membrane.

Finally, the invention comprises methods and pharmaceutical or cosmetic compositions for influencing cellular aging or treating diseases in humans, mammals, or other vertebrates in which anti-SCA IgG plays a role. A pharmaceutically or cosmetically effective amount of the synthetic SCA or one of the component peptides is administered to the host to partially or completely block the activity of the antibodies. The pharmaceutical or cosmetic compositions comprise an effective amount of the synthetic SCA or a component peptide in a pharmaceutically or cosmetically acceptable carrier. Alternatively, the synthetic SCA or component peptide can be administered in such a way as to increase the immune response in the host. Preferably, this is accomplished by targeting the SCA or peptide to a particular type of cell.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1A-1D shows the cDNA and inferred amino acid sequence of the human erythrocyte membrane anion-transport protein (band 3).

FIG. 2A-2B shows the inhibition of senescent cell IgG binding to erythrocytes by synthetic peptides or synthetic peptide mixtures. Competitive inhibition studies were performed as described in Example 1 at the concentrations indicated on the graph. For peptide mixtures, the total peptide used was the amount indicated with each peptide constituting half of that amount. 2A. (▲) CYTO (R139-159); (●) ANION 1 (R538-554); (◯) COOH (R812-827); (X) ANION 1 and COOH mixture. B (●) COOH hexamer (N6) consisting of 6 amino acids on the amino side of COOH; (x) COOH hexamer (N6) and ANION 1 mixture; (◯) GLYCOS (R630-648); (▲) ANION 2 (R588-602). The data for peptides ANION 1, COOH, and their admixtures are the averages of three separate inhibition experiments, each of which consisted of replicative determinations. Lines were fitted by the method of least squares. The data of ANION 1 and COOH could be fitted by a single line in FIG. 2A. Other COOH subpeptides gave the following percent inhibition: R818-827 (17M, 12.2 ug), 54±7; R818-823 (17 M, 6.9 ug), 27±4; R822-827 (70.6 M, 30 ug), 30±2.

FIG. 3 is a model of membrane associated and external regions of anion transport protein band 3.

FIG. 4A and 4B shows "walking" the band 3 molecule to localize the active aging antigenic site using binding of SCIgG to synthetic peptides as determined by immune labeling of electrophoretic blots. FIG. 4A shows polyacrylamide gels of peptides stained with Coomassie blue R followed by silver stain. FIG. 4B shows an autoradiograph of immunoblot incubated with IgG autoantibody from senescent erythrocytes.

The peptides and their residue number are: A. CYTO, 129-144, AGVANQLLDRFIFEDQ; B. 426-440, LLGEKTRNQMGVSEL; C. 515-531, FISRYTQEIFSFLISLI; D. 526-541, FLISLIFIYETFSKLI; E. ANION 1, 538-554, SKLIKIFQDHPLQKTYN; F. 549-566, LQKTYNYNVLMVPKPQGP; G. 561-578, PKPQGPLPNTALLSLVLM; H. 573-591, LSLVLMAGTFFFAMMLRKF; I. ANION 2, 588-602, LRKFKNSSYFPGKLR; J. 597-614, FPGKLRRVIGDFGVPISI; K. 609-626, GVPISILIMVLVDFFIQD; L. 620-636, VDFFIQDTYTQKLSVPD; M. GLYCOS, 630-648, QKLSVPDGFKVSNSSARGW; N. 645-659, ARGWVIHPLGLRSEF; O. 776-793, MEPILSRIPLAVLFGIFL; P. 789-805, FGIFLYMGVTSLSGIQL; Q. 800-818, LSGIQLFDRILLLFKPPKY; R. COOH, 812-827, LFKPPKYHPDVPYVKR; and S. 822-839, VPYVKRVKTWRMHLFTGI.

FIG. 5 shows the inhibition of senescent cell IgG binding to erythrocytes by the band 3 synthetic peptide COOH, or COOH with the lysines substituted with glycines (COOH—G) or arginines (COOH—R).

FIG. 6 shows the inhibition of anion transport by band 3 synthetic peptides. Equimolar amounts of sulfate and band 3 peptides were used. *P≦0.05; P≦0.001; *P≦0.001 compared to control without peptide.

Peptides used for "walking" COOH were: 789-805, FGIFLYMGVTSLSGIQL; 804-811, QLFDRILL; COOH, 812-827, LFKPPKYHPDVPYVKR; 813-818, FKPPKY; 818-823, YHPDVP; 818-827, YHPDVPYVKR; 822-827, VPYVKR; 822-839, VPYVKRVKTWRMHLFTGI; 828-834, VKTWRMH; R830-835, TWRMHL; and 832-837, RMHLFT.

FIG. 7 shows inhibition of erythrocyte anion transport by band 3 synthetic peptide COOH, or COOH with the lysines substituted with glycines (COOH—G) or arginines (COOH—R).

DETAILED DESCRIPTION OF THE INVENTION

Figure 2A:
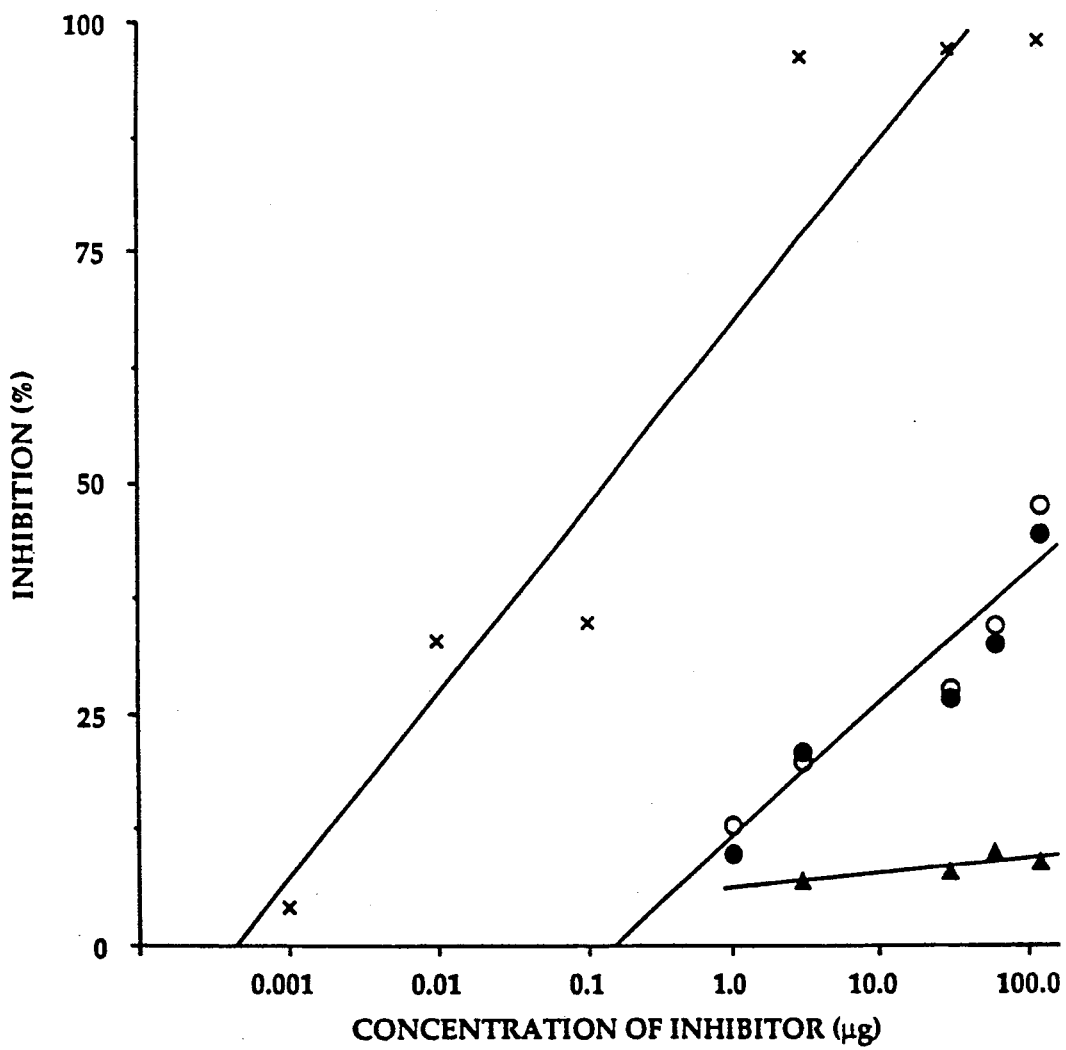

Reference will now be made in detail to the presently preferred embodiments of the invention, which, together with the following examples, serve to explain the principles of the invention.

The invention relates to a synthetic senescent cell antigen (SCA) and the peptides comprising it. The antigen is comprised principally of two peptides immunoreactive with antibodies to naturally occurring SCA (IgG autoantibody), which bind to old cells. As used herein, the term "peptide" means a molecule comprised of up to 40 amino acids linked by peptide bonds.

One of these peptides, which we refer to as ANION 1, is encoded by the nucleotide sequences 1612–1662 as shown in FIG. 1, which shows the nucleotide sequence and the derived amino acid sequence of human band 3. These correspond to amino acids 538–554. Thus, ANION 1 comprises the amino acid sequence SKLI-KIFQDHPLQKTYN (Ser-Lys-Leu-Ile-Lys-Ile-Phe-Gln-Asp-His-Pro-Leu-Gln-Lys-Thr-Tyr-Asn).

The second principal peptide, which we call COOH, is encoded by the nucleotide sequences 2434 to 2481 as shown in FIG. 1A–1D, which corresponds to amino acids 812–827. Thus, COOH comprises the amino acid sequence LFKPPKYHPDVPYVKR (Leu-Phe-Lys-Pro-Pro-Lys-Tyr-His-Pro-Asp-Val-Pro-Tyr-Val-Lys-Arg).

The peptides of the invention are at least substantially pure and preferably pure. As used herein, the term "substantially pure" and similar terms means that the peptide is at least 90% pure by weight. That is, the peptides do not contain more than 10% by weight of chemicals other than the peptide. As used herein, the term "pure" and related terms means that the peptide is at least 95% pure by weight and preferably at least 99% pure by weight.

The peptides of the invention act together synergistically to mimic the effect of naturally occurring SCA. Thus, the synthetic SCA of the invention is a mixture of substantially purified or purified peptides, which are separately immunoreactive with antibodies to SCA. Preferably, those peptides are ANION 1 and COOH in a proportion of about 90% to 10% to about 10% to 90%, preferably about 50% to 50% and most preferably about 40% to 60% ANION 1:COOH by weight.

The peptides of the invention can also be chemically linked to form the synthetic SCA. A number of methods are feasible for the formation of a covalent assembly that mimics the potent synergistic effect of the admixture of ANION 1 and COOH. One approach is to synthesize a modified ANION 1 by addition of a C-terminal CYS and a modified COOH by addition of an N-terminal CYS. A disulfide-bonded peptide consisting of the form ANION-1-S-S-COOH will result following admixture and purification by High Performance Liquid Chromatography. Another approach is to use "walking" procedures described herein to identify shorter (6–10 amino acids) internal stretches of ANION 1 and COOH (e.g. peptide N6) that bind anti-SCA IgG autoantibody and show the capacity for synergism. A single peptide of 16–20 amino acid residues can be synthesized to contain these regions in the proper order. If necessary, spacers, such as glycines, can be inserted between the two peptides to ensure proper folding.

ANION 1 and COOH are described with reference to particular amino acid sequences and particular positions on human band 3. Given the teachings described here, a person skilled in the art could derive analogous peptides from the SCA of other animals. Such a person could also use known techniques, involving group specific reagents to modify particular amino acids, to modify or construct peptides that differ slightly in the type or sequence of amino acids as compared to ANION 1 and COOH, yet function analogously to them. Such techniques are disclosed in *Guide to Protein Purification*, M. P. Deutscher, ed. (Special reprinting of *Methods in Enzymology*, Vol. 182) Academic Press, New York, 1990, incorporated herein by reference. Moreover, such a person could use such techniques to modify the peptides disclosed herein to enhance their activity. Thus, it is possible for a person of ordinary skill in the art to conceive of and derive a class of synthetic SCA and component peptides having common elements of structure and mechanism of action and differing from one another in only a few amino acid residues, once the principal members of such class, ANION 1, COOH, and the synthetic SCA comprised of ANION 1 and COOH, were identified by the teachings of the present invention. Accordingly, such modified, analogous, or enhanced peptides and synthetic SCAs are encompassed within the scope of this invention, provided they are immunoreactive with antibodies to naturally occurring SCA.

The peptides of the invention are synthesized by any technique known in the art that can be used to synthesize peptides of approximately 16–17 amino acids in length. The current method of choice is based upon the solid phase peptide synthesis procedures of Merrifield (Merrifield, R. B. (1981), "Current Methods in Solid Phase Peptide Synthesis," in *Chemical Synthesis and Sequencing of Peptides and Proteins*. Liu, T., Schecter, A., Heinrikson, R. and Condliffe, P., eds., Elsevier/North-Holland, Amsterdam, pp. 41–52) (incorporated herein by reference) and is usually carried out using automated solid phase peptide synthesizers.

The synthetic SCA and component peptides will be useful in a wide variety of applications and fields. These include scientific research, clinical diagnosis, treatment of diseases, and the purification of air and water.

The synthetic SCA and peptides can be used in a wide variety of scientific experiments and areas of research. Basically, they can be used in any method or technique involving or requiring the inhibition of the binding of senescent cell IgG to senescent cells in vitro or in vivo. An amount of the synthetic SCA or one of the peptides sufficient to inhibit the binding of senescent cell IgG is administered to the in vitro or in vivo system. The amount and conditions of administration can be determined by routine experimentation by one skilled in the art, given the teachings herein.

The products of the invention can be used to examine various physiological, biochemical, and immunological mechanisms in humans and other animals, such as those relating to the following:

1. Cellular aging, degeneration, and life span;
2. Removal of senescent cells;
3. Anion transport across cellular membranes;
4. Disease mechanisms where increased senescent cell IgG may play a role, such as hemolytic anemia, sickle cell anemia, and idiopathic thrombocytopenia purpura;
5. Other autoimmune disease mechanisms, such as rheumatoid arthritis and systemic lupus erythematosus; and 6. Other disease mechanisms, such as those involved in malaria and cancer.

A composition in accordance with the present invention useful as an investigational reagent contains an amount of the synthetic SCA or peptides of the invention sufficient to provide information and data when used in an in vitro or in vivo system containing anti-SCA antibodies. The determination of the amount of SCA or peptide necessary to accomplish a particular research goal depends upon the specific types of investigation involved, and it is readily within the skill of one carrying out such research.

The antigen and component peptides can be used in diagnostic assays to detect or measure antibodies to SCA in biological samples, such as tissue or blood, from humans and other animals. A sample suspected of containing such antibodies is contacted with the peptides or the synthetic SCA for a sufficient period of time and under appropriate conditions known to those skilled in the art for an immunological reaction to occur, whereby the antigens bind to the antibodies. A determination is then made as to whether or not the immunological reaction has occurred, using methods and techniques known to those in the art. The degree of the reaction can also be determined, providing a measurement of the antibodies in the sample. The peptides and antigen can be used in various immunoassays where they are utilized in liquid phase or bound to a solid phase carrier. In addition, they can be detectably labeled in various ways for use in such immunoassays. The immunoassays include, but are not limited to, radioimmunoassays, Western blot, enzyme-linked immunosorbent assays (ELISA), immunofluorescent assays, chemiluminescent assays, or bioluminescent assays. The various detectable moieties that can be used to label the peptides and antigens of the invention, techniques for doing so, and the various specific assays and conditions for using them are well-known to those skilled in the art. For example, see U.S. Pat. No. 4,486,530 to David, et al., issued Dec. 4, 1984, U.S. Pat. No. 4,708,818 to Montagnier, et al., issued Nov. 24, 1987, and U.S. Pat. No. 4,753,873 to Beltz, et al., issued Jun. 28, 1988, all of which are incorporated herein by reference.

The invention also comprises kits for scientific research or clinical diagnosis. The kit is a container holding the peptides or synthetic antigen of the invention and a means for detecting or measuring an immunological reaction between the peptides or antigens and the antibodies to SCA. Preferably, such means comprises a detectably labeled antibody to such antibodies (such as goat anti-IgG labeled with peroxidase) or a detectably labeled antibody to the antigen or peptides.

The invention also comprises a method for removing anti-SCA antibodies from a solution by running the solution through an affinity column in which the synthetic SCA or a component peptide is coupled to a solid phase matrix to serve as an immunoadsorbent. The peptides, in an antigenically-stable form, are coupled covalently to epoxy-activated Sepharose (Sepharose-4B, Pharmacia) as described by Schluter and Marchalonis, *Proc. Natl. Acad. Sci. USA*, 83:1872-1876 (1986), incorporated herein by reference.

Another application for the antigen and peptides of the invention relates to methods and apparatus for transferring or trapping anions. COOH and another peptide that we also synthesized as described in Example 1, ANION 2, bind to virtually any anion. Therefore, they can be used to trap or remove anions from various gases, solutions, or other systems, or they could be used in the differential transfer of such anions. For example, they could be incorporated into natural or synthetic membranes, barriers, or synthetic anion pumps. The process of incorporation into synthetic membranes occurs by methodology similar to that used for the preparation of liposomes as disclosed in Szoka, F. and Papahadjopoulos, D. (1981), "Liposomes: Preparation and Characterization", in *Liposomes: From Physical Structure to Therapeutic Applications* (Knight, C. G., ed,) Elsevier/North-Holland, Amsterdam, pp. 51-82, incorporated herein by reference. The antigen and peptides can be used to separate anions from various media. For example, they could be used alone or coupled to soluble or insoluble matrices to separate anions in solution. This would have application, for example, in the purification of seawater. In addition, the products of the invention could be used for anion removal or exchange from air. One application for such air purification would be found in closed systems such as a space shuttle.

In a preferred embodiment, this can be carried out using peptides coupled covalently to an insoluble matrix such as Sepharose (specially prepared agarose) for use in a fluid medium or to a solid matrix such as polystyrene or polycarbonate for use in air. The insoluble matrix is preferably in an affinity column. Peptides can be bound tightly to stable plastic matrices by addition of the peptides in a fluid medium and then drying down the solution by gentle heating at 37° C. according to the method of Ross, C. R., Hubbard, R. A., Schluter, S. F., Diamanduros, A., Wang, A. C. and Marchalonis, J. J., (1989) *Immunologic Research* 8:81-97, incorporated herein by reference. For use as an anion trap, a large surface of peptide-derivatized matrix would be required, so fibers or powders would be used.

Accordingly, the invention includes a method for separating anions from a gas or a liquid containing the anions (i.e., a solution) by contacting a sufficient amount of the peptide or synthetic antigen of the invention with the gas or the liquid to form complexes between the antigen or peptides and the anions. The complexes are then separated from the gas or liquid by means known in the art. Preferably, the antigen or peptide is bound to an insoluble matrix, as in an affinity column. Alternatively, they are bound to a membrane, which is in contact with the gas or the liquid.

Another application of the products of the invention would be in altering or increasing the storage life of blood. SCA triggers the removal of stored red blood cells. An effective amount of the antigen or peptide would be added to stored blood to inhibit the binding of anti-SCA IgG. Alternatively, the blood could be contacted with the synthetic SCA or a component peptide attached to an insoluble matrix for a period of time sufficient to remove all or substantially all of the autoantibody. The blood would then be recovered.

The antigen and peptides of the invention are also expected to have utility as pharmaceuticals and cosmetics. Synthetic senescent cell antigen blocks the biological activity of physiologic autoantibodies that initiate removal of senescent cells in vitro. We hypothesize that this antigen can be used to prevent cell destruction and disease, and that it can be used to manipulate cellular life span in situ. This latter hypothesis can be tested through site specific mutagenesis of the aging antigenic sites. Thus, the use of these products internally or externally on humans and other animals can be expected to influence cellular aging, degeneration, and life span. They can also be expected to influence the autoimmune response and, therefore, find utility in treating diseases where SCA and anti-SCA IgG play a role. Synthetic senescent cell antigen might also be effective in preventing or inhibiting erythrocyte and platelet destruction in vivo in diseases such as autoimmune hemolytic anemias and idiopathic thrombocytopenia purpura, which may be caused by higher than normal amounts of anti-SCA IgG. Thus, the invention includes a method for influencing cellular aging and degeneration, influencing the autoimmune response, and treating diseases caused by an increased level of anti-SCA IgG in humans and other animals, particularly mammals, by using the antigen and peptides of the invention to block the biological activity of the autoantibodies that initiate the removal of senescent cells. A pharmaceutically effective amount of these materials are administered to the animal host in need of treatment.

To remove antibodies to SCA, peptides or synthetic SCA in soluble form could be injected into the individual. Alternatively, a form of plasma pheresis could be used wherein the person's plasma is circulated through an insoluble matrix containing the peptide(s) or synthetic SCA to remove antibodies to SCA. Preferably, the insoluble matrix is in an affinity column. This is useful for autoimmune diseases in which it is desirable to remove antibodies to SCA.

For diseases in which it is desirable to increase the immune response, such as cancer, soluble forms of synthetic SCA could be injected alone or with a carrier to make them more immunogenic. Injections would be, for example, intradermal or subcutaneous with a multiple injection protocol. The synthetic SCA can be targeted to particular types of cells by techniques known in the art. For example, it could be coupled to a monoclonal antibody specific to the particular cell. Alternatively, it could be coupled to poly-L-lysine, which binds to cell membranes.

SCA coupled to an insoluble matrix could be used to absorb antibody to SCA from human or autologous plasma. It could be injected for increased removal of cells or to prepare Fab fragments to bind antigen on cells and thus decrease removal (e.g. storage).

Generally, these materials are administered in a pharmaceutically compatible carrier. Accordingly, the invention encompasses a pharmaceutical composition for the treatment or amelioration of diseases caused by elevated levels of anti-SCA antibody in animals, particularly mammals, and most particularly humans, comprising an effective amount of the antigen or peptides of the invention for such treatment or amelioration in a pharmaceutically or other acceptable carrier.

It is contemplated that pharmaceutical preparations containing synthetic SCA can be administered locally, as by injection or topical application, intravenously, orally, intradermally, subcutaneously, intraocularly, subconjunctively, intramuscularly, and intrathecally. The mode of administration will necessarily depend upon the disease involved.

The amount of antigen or peptide to be administered would depend upon the particular disorder being treated. Such a determination is routinely made by those of ordinary skill in the art in determining therapeutic dosages and is within the scope of tasks routinely performed by them without undue experimentation.

The compounds of the invention may also be useful in cosmetic preparations because of their potential anti-aging activity. Thus, the invention encompasses cosmetic compositions comprising a cosmetically effective amount of the synthetic SCA or a peptide of the invention in a cosmetically acceptable carrier.

Pharmaceutical and cosmetic compositions are prepared by techniques known in the art, given the teachings contained herein. The peptides or synthetic SCA are mixed with the additives customary for this purpose, such as vehicles, stabilizers, solubilizers, or inert diluents, and converted by customary methods to a suitable administration form, such as tablets, capsules, solutions, suspensions, and emulsions.

It is to be understood that application of the teachings of the present invention to a specific problem or environment will be within the capabilities of one having ordinary skill in the art in light of the teachings contained herein. Examples of the products of the present invention and processes for the use appear in the following examples.

EXAMPLE 1

Localization And Primary Structure Of Senescent Cell Antigen

We constructed and tested synthetic peptides to identify aging antigenic sites on band 3 using a competitive inhibition assay and immunoblotting with IgG directed against the aging antigen on old cells. Results indicate that: a) the active antigenic sites of the aging antigen reside on membrane protein band 3 residues which are extracellular regions implicated in anion transport (residues 538–554 and 788–827); b) a putative ankyrin binding region peptide is not involved in senescent cell antigen activity; and c) carbohydrate moieties are not required for the antigenicity or recognition of senescent cell antigen since synthetic peptides alone abolish binding of senescent cell IgG to erythrocytes. One of the putative transport sites that contributes to the aging antigen is located toward the carboxyl terminus. A model of band 3 is presented. Localization of the active antigenic site on band 3 molecule will facilitate definition of the molecular changes occurring during aging that initiate molecular as well as cellular degeneration.

Materials and Methods

Sodium dodecyl sulfate ($NaDodSO_4$) polyacrylamide gel electrophoresis and immunostaining of peptides. Peptides were analyzed on 6–25% or 12–25% linear gels (6, 7, 27–29). Immunoautoradiography was performed by immunoblotting as described previously (6, 7, 28–30). Immunoblots were exposed to Kodak Ortho G (OG-1) film at −70° C. using our standard procedures (30, 45).

IgG binding and inhibition assay. IgG was isolated from senescent RBC from 50 liters of blood and purified with Protein A Sepharose as previously described (2, 4). IgG eluted from senescent cells (SCIgG), rather than serum IgG, was used because normal serum contains antibodies to spectrin, actin, 2.1, etc. (28). Competitive inhibition studies were performed using synthetic peptides to absorb the IgG isolated from senescent erythrocytes. Intact dimeric, senescent cell IgG containing Fc portion binds to senescent cells in situ and initiates their removal (1–7, 30). Fab fragments were not used because we were simulating the physiological situation. IgG isolated from aged erythrocytes binds specifically to senescent cells. For example, IgG eluted from young control erythrocytes does not bind to senescent cells (2, 30). Moreover, the specific binding capacity of the autoantibody was eliminated by absorption with purified senescent cell antigen (SCA; 7). SCIgG (3 ug) was absorbed with synthetic peptides at the concentrations indicated or purified SCA, as a control, for 60 min. at room temperature, and incubated with stored red cells for 60 min. at room temperature (1, 2, 4, 30). Storage mimics normal aging in situ immunologically and biochemically (1-7, 30). The number of red cell-bound IgG molecules was quantitated before and after absorption using equilibrium binding kinetics (7, 30, 31). Details of the methods are given elsewhere (27). Percent inhibition was calculated from the following formula: 100[1-(x-b/T-b)] where x=molecules of IgG autoantibody bound per cell; T=total number of IgG antibody molecules bound in the absence of inhibitor; b=background Protein A binding.

Peptides. Peptides were prepared by solid phase synthesis using an Applied Biosystems 430A automatic peptide synthesizer. They were analyzed by amino acid analysis, HPLC, sequencing, and/or FABS to determine purity. Amino acids are referred to by the standard single letter code. Peptides that are not soluble in phosphate buffered saline were dissolved in 1-2% NaDodSO$_4$. Others were solubilized in acetic acid or trifluoroacetic acid, and sodium dodecyl sulfate (1-2%) is added. Once the peptides were in solution, they were conjugated to ovalbumin (5X crystallized) or BSA with 0.02% glutaraldehyde (32). The reaction was allowed to proceed for 30-60 min. blocked with ethanolamine, and the conjugate dialysed against PBS in tubing with a molecular weight cut off of $\leq$1000. NaDodSO$_4$ did not interfere with the glutaraldehyde coupling reaction. Since our assays included bovine serum albumin (BSA), the inclusion of albumin did not alter the assay.

Computer analysis. Sequence and protein structural analyses were performed using programs of the Genetics Computer Group (GCG), University of Wisconsin, Sequence Analysis Software Package (33).

Results and Discussion

Identification of the aging antigenic site(s). We concluded from previous studies that senescent cell antigen is a degradation product of band 3 that includes most of the ~35,000 Da carboxyl terminal segment and the ~17,000 Da anion transport region (5). Both immunoblotting studies with IgG isolated from senescent cells and peptide mapping studies of senescent cell antigen indicated that senescent cell antigen lacks a ~40,000 molecular weight cytoplasmic segment which contains the amino terminus and, possible, additional peptides of band 3 (5-7). Peptide mapping studies and anion transport studies suggested that a cleavage of band 3 occurs in the anion transport region (5). Furthermore, breakdown products of band 3 are observed in the oldest cell fractions but not in young or middle-aged cell fractions, and anion transport is impaired in old cells (5-7, 30).

We deduced that cleavage of old band 3 occurred approximately a third of the way into the transmembrane anion transport region from the carboxyl terminus end. Therefore, we synthesized peptides of erythrocyte band 3 that we speculated might have anion transport activity. Peptides were synthesized based on the human sequence data from the paper by Tanner, et al. (34). We selected one anion transport segment which appeared to be exposed to the outside of the cell and one that is further along the molecule towards the amino terminus and outside the region that we speculated was included in senescent cell antigen (5). The first peptide (ANION 1, position 538-554: SKLIKIFQDHPLQKTYN) included two important amino acids. The lysine at 539 is a covalent binding site for the anion transport inhibitor, diisothiocyano dihydrostilbene disulphonate (DIDS), and the tryosine at residue 553 is radioiodinated by extracellular lactoperoxidase (34). The second peptide (ANION 2, 588-602: LRKFKNSSYFPGKLR) is situated toward the end of the region and is probably intracellular because the potential N-glycosylation site at ASN-593 is not glycosylated (34). We speculated this peptide would lack inhibitory activity because it would not be presented as an antigen on native band 3. The last peptide from the carboxyl terminus region (COOH, 812-827: LFKPPKYHPDVPYVKR) contained both hydrophobic and hydrophylic regions. The lysines found in this region may comprise another binding site for DIDS (35). As a control, we used a peptide from the cytoplasmic segment of band 3 within the region of the putative ankyrin binding site (36) (CYTO, 129-144: AGVANQLLDRFIFEDQ). As an additional control, a peptide containing the N-glycosylation site that is glycosylated (GLYCOS, 630-648: QKLSVPDGFKVSNSSARGW), was included because it is extracellular.

Competitive inhibition studies were performed using synthetic peptides to absorb the IgG isolated from senescent erythrocytes. IgG binding and inhibition were determined with a protein A binding assay. This biological assay measures the fate of erythrocytes in vitro and in vivo (1, 2, 4).

Figure 2B:
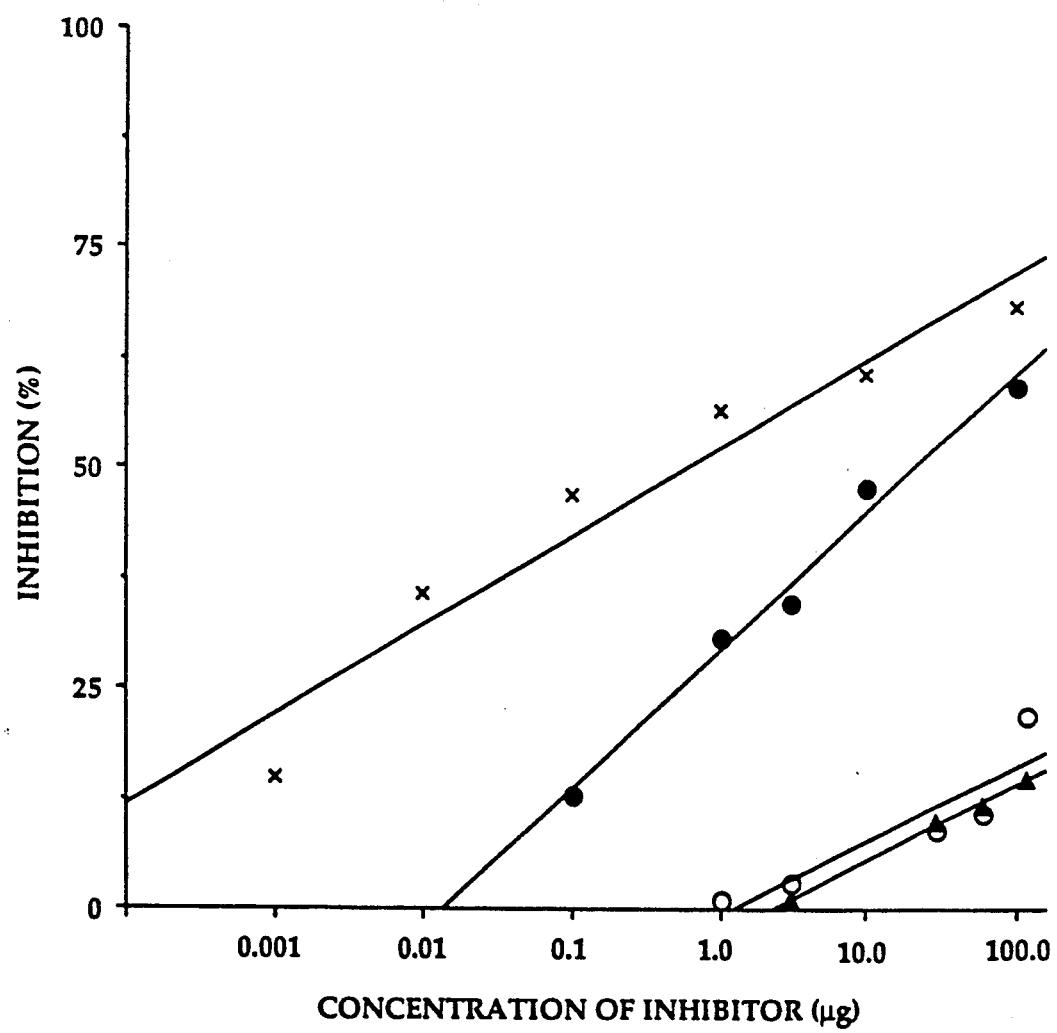

Results of these studies suggest that senescent cell IgG recognizes antigenic determinants that lie within a putative anion transport region 538-554 and a transport site containing a cluster of lysines toward the carboxyl terminus, 812-827 (Table 1). ANION 2 is only weakly inhibitory and CYTO does not inhibit. The competition inhibition data illustrated in FIG. 2 show that peptides ANION 1 and COOH are inhibitory over a range of 3 to 100 ug (FIG. 2A), whereas the internal peptide from the anion transport region (ANION 2) and a peptide from an external glycosylated site (GLYCOS) are only weakly inhibitory (FIG. 2B), and the putative ankyrin binding peptide does not react with the antibody (FIG. 2A).

For two reasons, we decided to mix the two inhibitory peptides to determine whether they acted synergistically. First, both are inhibitory, but the inhibition is not complete even at 300 ug. Second, the results of our earlier peptide mapping studies with topographically defined segments of band 3 suggested that senescent cell antigen was composed of peptides from both the anion transport transmembrane region and the 35,000-38,000 Da carboxyl terminal segment (5). Mixing of these two regions produced a peptide map that closely resembled senescent cell antigen even though it contained more peptides. The mixture of these two peptides produced ~50% inhibition at 0.1 ug (i.e. 0.05 ug of each peptide) indicating that ANION 1 and COOH interact together to form a three dimensional structure that functions as an aging antigen (FIG. 2A). COOH hexamer (N6) consisting of 6 amino acids on the amino side of COOH gave significant inhibition (~50% at 10 ug) but did not synergize as well with ANION 1 as did COOH itself since a ~10 fold increase in peptide is required to obtain inhibition (~50% inhibition at 1ug; FIG. 2B). COOH decamer (C10) consisting of 10 amino acids on the carboxyl side of COOH gave 54±3% inhibition at 30 ug. A mixture of ANION 2 and COOH did not exhibit synergy (inhibition: 18±4% at 30 ug).

Synthetic peptides would not be expected to be as effective as the native band 3 molecule itself because the short peptide segments do not assume the same tertiary configuration as that of the 911 amino acid band 3 molecule. The synergism of peptides ANION 1 and COOH suggests that the conformation of the determinants of these two peptides interacting with each other is similar to that of the intact aging antigen. These results, together with data indicating that DIDS crosslinks these two regions (35), suggest that these peptides lie in close spatial proximity in native, aged band 3. This is consistent with other data indicating that these two sites are in close proximity in native band 3 (24, 36, 37).

Binding of senescent cell IgG to ANION 1 and peptide COOH which is close to the carboxyl terminus of band 3 suggests that these segments are extracellular because the IgG molecule is 150,000 molecular weight and too large to enter a cell. This is consistent with the data of Jennings (35) which indicates that these regions are extracellular and that a segment located carboxyl to the trypsin cleavage site at lysine 743 and an S-cyanylation cleavage site ~7000 Da from the C-terminus is crosslinked by extracellular DIDS (35).

Results of these studies with synthetic peptides are consistent with the physiological data demonstrating that old erythrocytes have impaired anion transport (6, 7, 30), the biochemical and immunological data indicating that band 3 undergoes degradation with loss of a cytoplasmic segment during the aging process (5-7, 30), and the data derived from alterations and/or mutations of band 3 indicating that changes associated with accelerated aging involve changes in the anion transport region of band 3 (7, 38, 39).

Figure 3:
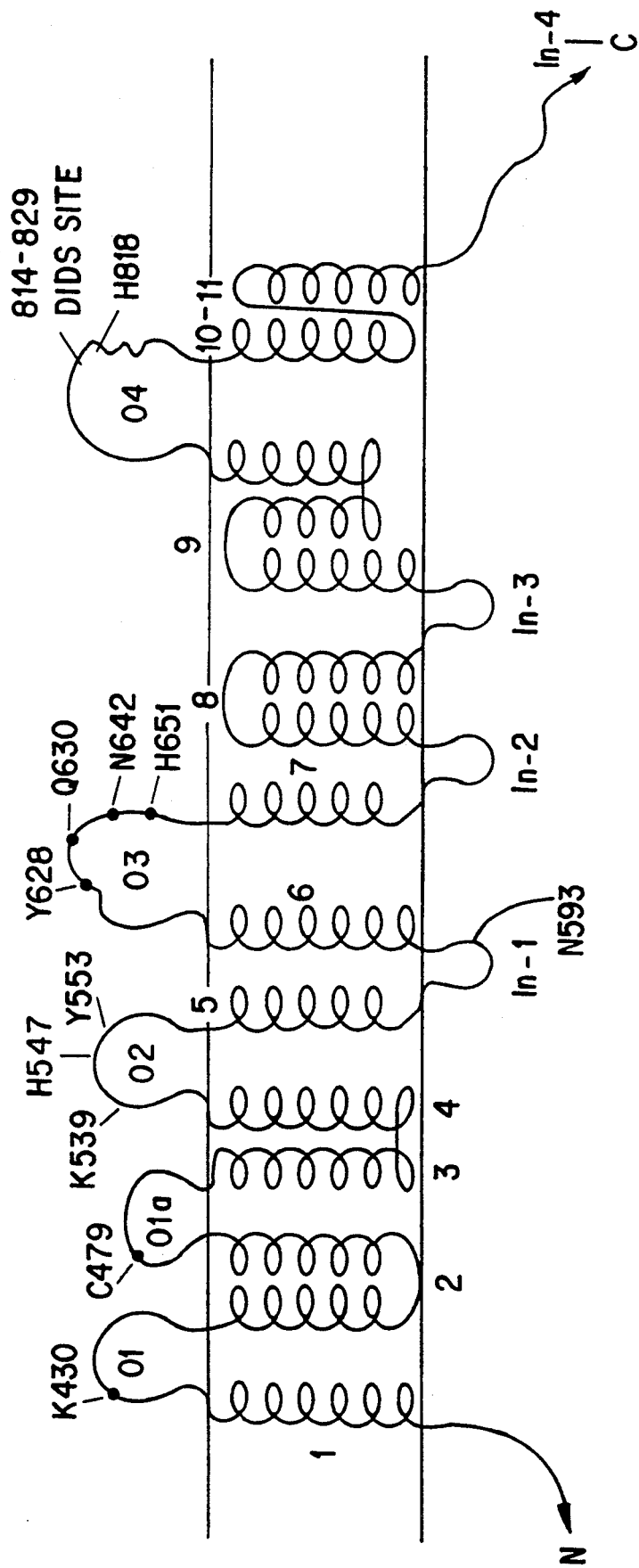

Model of the membrane associated region of human band 3. Based on the above and other considerations, we developed a working model for the membrane associated region of human band 3 protein, approximate residues 400-870. The model was constructed using the program PEPPLOT of the GCG package to identify membrane spanning nonpolar helices (40) and intervening hydrophilic loops (41). The location of the hydrophilic loops as extracellular or intracellular was predicted on the basis of established chemical or biological markers, e.g., the demonstration that residues 814-829 contain a DIDS binding site or the availability of Y553 for external radioiodination (34). These regions are assembled into a model in FIG. 3. Key residues are identified to facilitate their identification within the sequence. This is a two dimensional representation that does not reflect three dimensional associations of residues that are separated by long stretches of sequence. Our present results show, however, that close steric association must be maintained by external loops 02 and 04. If these regions are associated on the same band 3 monomer, then band 3 loops back upon itself so that these regions are contiguous. Alternatively, the functional assembly may be dimers in which close associations of 02 and 04 form between separate molecules. Our incorporation of recent human data (34) with the antigenic results presented here allows refinement and development of a model incorporating band 3 designated 04 that contains the peptide COOH and its component N6 which are potent inhibitors of the binding of autoantibodies to the aging antigen to red cells. All of the data support the external presentation of this region.

The short bilayer spanning segments may represent segments that enter the bilayer and exit again, looping back on themselves, without transversing the bilayer to the other side. These projections are based on hydrophobicity plots and may or may not exist in the membrane.

Amino acids that are exposed to the outside could reside on a hydrophobic helix within a membrane pore and still be accessible to the outside even though they are not on the outermost membrane. This probably applies to some band 3 sites designated as external although it is not reflected in the model. We suspect that the tertiary structure of band 3, when finally elucidated, will turn out to be a ring.

Computer search for regions of internal homology within band 3 was performed using programs COMPARE and DOTPLOT with a window of 30 residues and stringencies of 10.0 (low) and 15.0 (high). Homologies were disclosed among the membrane spanning nonpolar helical regions. For example, a segment of bilayer spanning helix adjacent to extracellular loop 02 had ~40% identity to a corresponding segment of bilayer spanning segment between internal loops 2 and 3; viz:

```
       460                    470
    |L L V V G| F S |G| P L L V |F| E E A F F |S|
    |L L V V G| M G |G| V A A L |F| G M P W L |S|
       710
```

Such relationships were not obvious among the hydrophilic regions; e.g. external hydrophilic loops 02 and 04 did not show significant sequence homology.

The reader is cautioned that a) models such as the one we have drawn are not accurate representations of the real world, and b) most, if not all, information on the location of functions on the band 3 molecule is based on circumstantial and indirect evidence.

Molecular "Walking" of band 3 to define the antigenic site. Our previous experiments suggest that the active antigenic sites of the senescent cell antigen reside on the peptides which we have designated ANION 1 and COOH. In this series of experiments, we attempted to confirm and define the active antigenic site by "walking" the anion transport domain of band 3 molecule which our studies indicate contain the antigenic determinants.

By "walking" we mean the antigenic analysis of a series of synthetic overlapping peptides that encompass the entire polypeptide chain adjacent to the active sites we have identified and include all predicted extracellular segments of band 3. The synthetic peptides are 17-19 mer and overlap their adjacent neighboring peptides by 6 residues in the overlap regions in order to optimize the feasibility of synthesis and to expect reasonable resolution of individual antigenic sites.

Peptides used for "walking" the molecule were: 515-531, FISRYTQEIFSFLISLI; 526-541, FLISLIFIYETFSKLI; ANION 1, 538-554, SKLIKIFQDHPLQKTYN; 549-566, LQKTYNYNVLMVPKPQGP; 561-578, PKPQGPLPNTALLSLVLM; 573-591, LSLVLMAGTFFFAMMLRKF; ANION 2, 588-602, LRKFKNSSYFPGKLR; 597-614, FPGKLRRVIGDFGVPISI; 609-626, GVPISI- LIMVLVDFFIQD; 620-636, VDFFIQD-TYTQKLSVPD; GLYCOS, 630-648, QKLSVPDGFKVSNSSARGW; 776-793, MEPILSRIPLAVLFGIFL; 789-805, FGIFLYMGVTSLSGIQL; 800-818, LSGIQLFDRILLLFKPPKY; COOH, 812-827, LFKPPKYHPDVPYVKR; 822-839, VPYVKRVKTWRMHLFTGI. In addition, we synthesized 2 predicted external sequences: R 426-440, LLGEKTRNQMGVSEL; and 645-659, ARGWVIHPLGLRSEF. The former sequence is not in a putative transport region. This was done to complete the testing of all predicted external band 3 sequences for senescent cell antigen since the antigenic determinants must be external to be accessible to the 150,000 molecular weight IgG molecule.

Figure 4A:
Figure 4B:
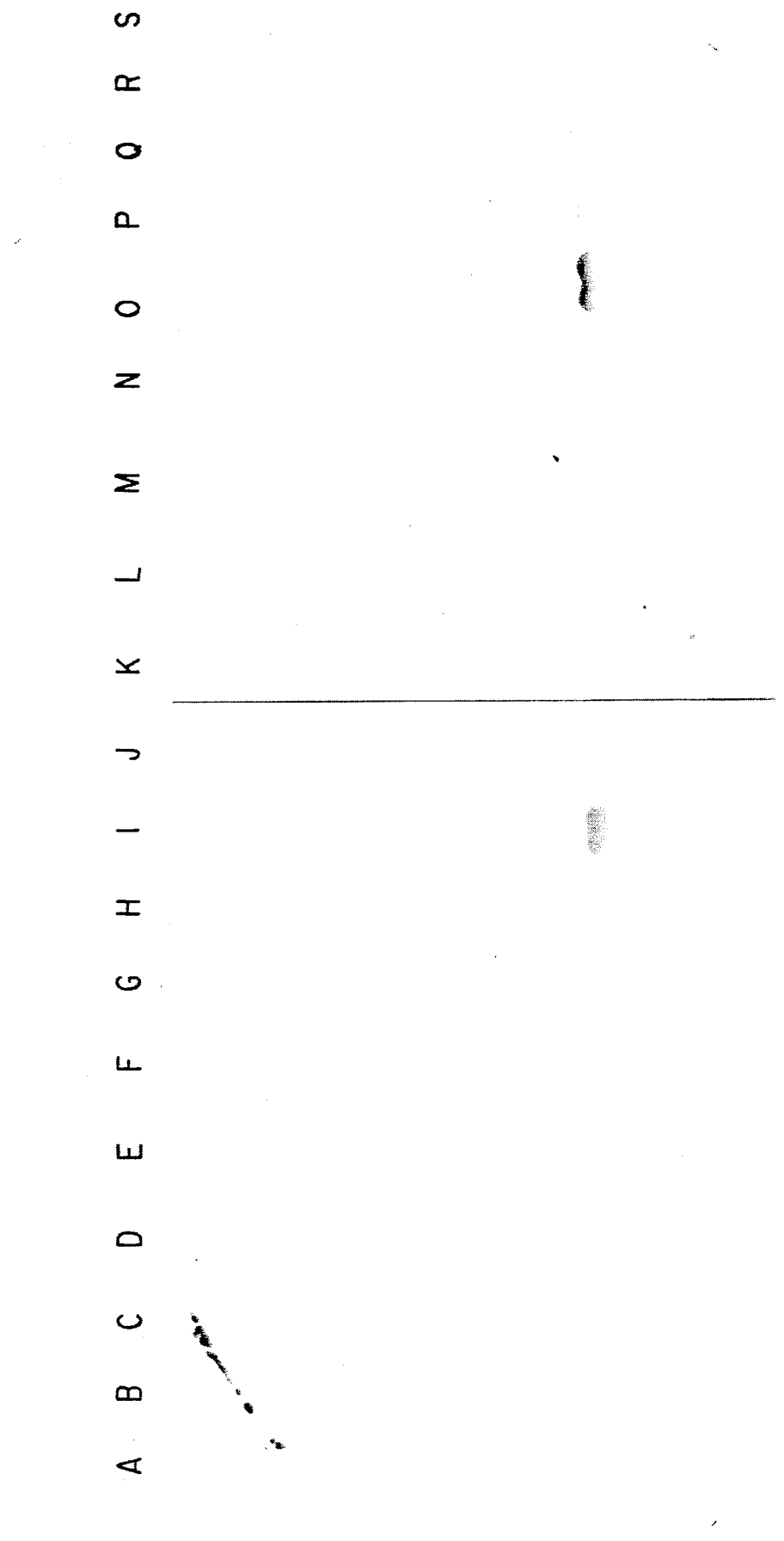
Figure 5:
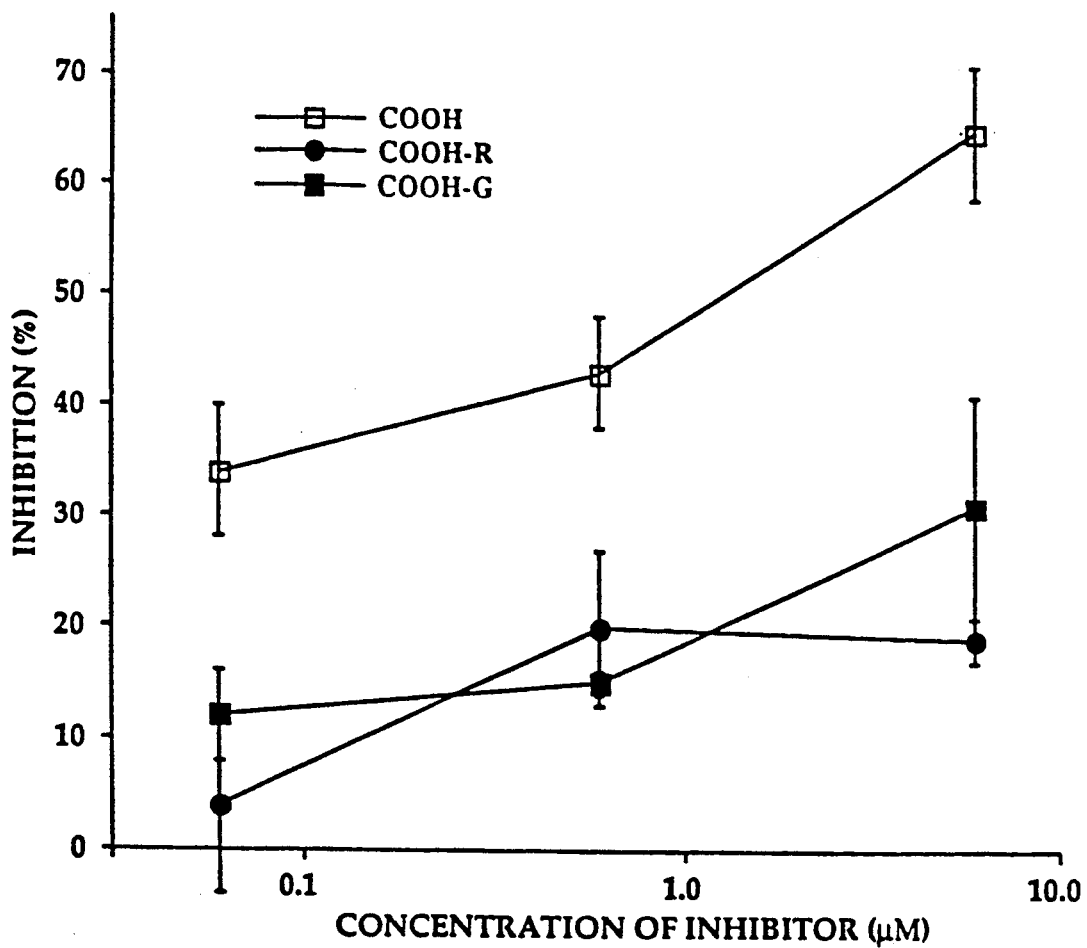

We used immunoblotting of the peptides followed by reaction with IgG eluted from senescent red cells (SCIgG) to localize the aging antigen site (FIG. 4A and B). We also used the IgG binding and inhibition assay at a singe concentration of peptide and performed Scatchard analysis (Table 2). We selected 30u for this "single concentration" assay because our two synergistic peptides, ANION 1 and COOH, give ≧95% inhibition at this concentration; whereas, "non-inhibitory" peptides give ≦20% inhibition. Peptides that were negative by immunoblotting were also negative in the inhibition assay (FIG. 4 and Table 2). We relied on immunoblotting with senescent cell IgG for peptides that were not completely soluble under physiologic conditions (FIG. 4).

Immunoblotting studies with senescent cell IgG showed binding to R 788-805, 800-818, in addition to COOH (R812-827). Peptides R788-805, 800-818 are to the amino side of COOH. R822-839, which has no labeling, is to the carboxyl side. R800-817 and 822-839 have 6 amino acids in common with COOH. Binding of antibody to R630-648 and trace binding to R645-659 was observed.

However, the competitive inhibition assay showed that significant inhibition of senescent cell IgG binding was obtained only with peptide R822-839 which is on the carboxyl side of COOH and contains 6 amino acids of COOH. Thus, its inhibitory effect may be due to the 6 common amino acids. Peptides 776-793, 788-805, and 800-839 were not completely soluble and were not tested in the cellular binding assay.

In the ANION 1 and ANION 2 peptide series, trace binding was observed in immunoblots to ANION 1 (R538-554) and the peptides to its amino (R526-541) and carboxyl (R549-566) side which have 6 amino acids overlap with that peptide. Senescent cell IgG bound to ANION 2 (R588-602) and, faintly, to the peptide to its carboxyl side (R597-614) which has 6 amino acids overlap.

The competitive inhibition assay showed that inhibition of 52±4% is obtained with R597-614. R526-543 and R549-566 could not be tested because of solubility. The peptide from external loop R426-440 was negative.

We used two approaches to determine the peptides with which autoantibody to senescent cell antigen reacts. The direct binding in Western blot analysis showed that the antibody bound to a number of peptides, including some that are internal and do not block in the cellular inhibition assay. This probably resulted from the fact that aged red cells that bind autoantibody are phagocytosed by macrophages and antigenic peptides are generated for presentation to T cells. These peptides are not exposed in the normal presentation of band 3 and senescent cell antigen on the erythrocyte surface, however. Our competitive inhibition studies showed that the native determinant is formed by interaction of two exposed peptide regions contributed by ANION 1 and COOH.

Thus, senescent cell antigen located is localized to a region within residues 538-554 and 788-827. Even though an antigen binding site is only 6 amino acids in size, these amino acids are probably not adjacent in primary structure. A minimal number of amino acids is probably required to generate the twists and turns necessary for the active three dimensional structure. The synergy between ANION 1 and COOH supports this. The data from the N terminus 6 amino acids of COOH indicate that even though significant inhibition can be obtained with a six mer peptide, larger quantities of the peptide are required, and synergy is impaired because ≧95% inhibition cannot be obtained at concentrations up to 100 ug. In contrast, ≧95% inhibition can be obtained with the mixture of ANION 1, and COOH at 10 ug, and, in some experiments, at 3 ug.

Studies indicate that the transport region of band 3 is highly conserved across tissues, individuals, and species (21, 27, 34, 42, 43). Since senescent cell antigen is generated on all cell types, tissues, and species examined (4), the regions that comprise senescent cell antigen must also be highly conserved both evolutionarily and in various tissues. In this study, we showed that active antigenic determinants of senescent cell antigen reside on peptides ANION 1 and COOH within residues 538-554 and 788-827. These peptides reside in highly conserved regions (34, 43).

We have localized senescent cell antigen, an aging antigen, in terms of primary structure. Localization of the active antigenic site of senescent cell antigen facilitates the next logical step, namely, definition of the molecular changes occurring during aging that initiate molecular as well as cellular degeneration and regulation of cellular lifespan. This will facilitate manipulation of cellular lifespan through site directed mutagenesis.

TABLE 1

| INHIBITION OF SENESCENT CELL IgG BINDING BY SYNTHETIC PEPTIDES OR SENESCENT CELL ANTIGEN[a] | |
|---|---|
| SAMPLE | INHIBITION (%) |
| BAND 3 PEPTIDE, CYTO | 0 |
| BAND 3 PEPTIDE, ANION 1 | 88 ± 7* |
| BAND 3 PEPTIDE, ANION 2 | 30 ± 12* |
| BAND 3 PEPTIDE, COOH | 99 ± 1* |
| SENESCENT CELL ANTIGEN | 54 ± 7* |

[a]Data are presented as the mean ± 1 SD of quadruplicate samples; *P ≦ 0.001 compared to the control. Senescent cell IgG (3 ug) incubated with peptides (300 ug) or buffer for 90 mins. at room temperature. Erythrocytes were added to the IgG and samples were incubated for 90 mins at room temperature. IgG on cells was quantitated using $^{125}$I-labeled Protein A.

TABLE 2

| "WALKING" OF BAND 3 PROTEIN TO DEFINE THE ANTIGENIC SITE: INHIBITION OF SENESCENT CELL IgG BINDING TO ERYTHROCYTES BY SYNTHETIC PEPTIDES OF BAND 3[a] | |
|---|---|
| SYNTHETIC PEPTIDE RESIDUE (#) | INHIBITION (%) |
| 426-440 | 11 ± 1 |
| 515-531 | 15 ± 1 |
| 526-541 | NT |
| 549-566 | NT |
| 561-578 | 0 |
| 573-591 | NT |
| 597-614 | 52 ± 4 |

TABLE 2-continued
"WALKING" OF BAND 3 PROTEIN TO DEFINE THE ANTIGENIC SITE: INHIBITION OF SENESCENT CELL IgG BINDING TO ERYTHROCYTES BY SYNTHETIC PEPTIDES OF BAND 3[a]

| SYNTHETIC PEPTIDE RESIDUE (#) | INHIBITION (%) |
|---|---|
| 609–626 | 12 ± 1 |
| 620–637 | NT |
| 630–648 | 9 ± 0 |
| 645–659 | NT |
| 776–793 | NT |
| 788–805 | NT |
| 800–818 | NT |
| 822–839 | 35 ± 2 |

[a]Data are presented as the percentage inhibition ± standard deviation of the binding of human autoantibody to senescent cell antigen. All peptides were tested at 30 ug. NT, not tested in the competitive inhibition assay because the peptide was not completely soluble in physiologic solutions even when coupled to BSA.

antigen. All peptides were tested at 30 ug. NT, not tested in the competitive inhibition assay because the peptide was not completely soluble in physiologic solutions even when coupled to BSA.

EXAMPLE 2

Contribution of Lysine to Antigenicity and Anion Transport

As shown in Example 1, the active antigenic sites of senescent cell antigen have been localized on band 3 membrane protein to residues number 538–554 and 812–827 through the use of synthetic peptides. Band 3 peptides tested were CYTO, 129–144: AGVANQLLD-RFIFEDQ; 426–439, LLGEKTRNQMGVSEL; 515–531, FISRYTQEIFSFLISLI; 526–541, FLIS-LIFIYETFSKLI; ANION 1, 538–554, SKLI-KIFQDHPLQKTYN; 549–566, LQKTYNYNVLMVPKPQGP; 561–578, PKPQGPLPNTALLSLVLM; 573–591, LSLVLMAGTFFFAMMLRKF; ANION 2, 588–602, LRKFKNSSYFPGKLR; 597–614, FPGKLRRVIGDFGVPISI; 609–626, GVPISI-LIMVLVDFFIQD; 620–636, VDFFIQD-TYTQKLSVPD; GLYCOS, 630–648, QKLSVPDGFKVSNSSARGW; 645–659, ARG-WVIHPLGLRSEF; 776–793, MEPILSRIPLAVL-FGIFL; 789–805, FGIFLYMGVTSLSGIQL; 800–817, LSGIQLFDRILLLFKPPKY; COOH, 812–827, LFKPPKYHPDVPYVKR; 822–839, VPYVKRVKTWRMHLFTGI. Peptides were tested both by immunoblotting with IgG autoantibody from old erythrocytes ("senescent cell IgG") and in a competitive inhibition assay with senescent cell IgG.

Results of that study indicate that the active antigenic sites of the aging antigen reside on membrane protein band 3 residues 538–554 and 778–827 which are extracellular, putative anion transport regions of band 3. Two peptides within these regions, ANION 1 (SKLI-KIFQDHPLQKTYN) and COOH (LFKPPKYHPD-VPYVKR), interact synergistically to generate a synthetic aging antigen that results in 98% inhibition of senescent cell IgG binding at 3 ug and causes 50% inhibition at 0.1 ug. Neither of these peptides alone gives greater than 50% inhibition at concentrations as high as 100 ug. In addition, our synthetic peptide studies show that a putative ankyrin binding region peptide (CYTO, residues 129-144) is not involved in senescent cell antigen activity, and carbohydrate moieties are not required for the antigenicity or recognition of senescent cell antigen since synthetic peptides alone abolish binding of senescent cell IgG to red cells. One of the putative transport sites that contributes to the aging antigen is located toward the carboxyl terminus. The active antigenic determinants of senescent cell antigen reside on highly conserved regions of band 3.

The peptides ANION 1 and COOH correspond to extracellular regions of band 3 containing lysines which are implicated in anion transport. In the present study, we defined the aging antigenic site by identifying lysine as a critical amino acid for antigenicity. The contribution of lysine to the antigenicity of the aging antigen and to anion transport was examined by chemically modifying the lysines on both synthetic peptides and whole cells, and by synthesizing peptides in which glycines or arginines were substituted for lysines. Anion transport sites were localized using 16–18 mer peptides followed by 6–8 mer peptides. Functional studies with the peptides COOH and ANION 1 indicated that they contain sulfate binding sites and inhibit sulfate transport in addition to carrying aging antigenic determinants. Substitution of arginines for lysines in COOH maintained the sulfate binding properties of the peptide; whereas, substitution of glycine for lysine did not. Residues 812–827 (COOH) and 813–818 (N6, the 6 amino acids on the amino side of COOH) were potent inhibitors of anion transport when used in equimolar amounts with sulfate, suggesting that these regions may be transport regions in situ.

Results of this study indicate that: (a) lysines are required for the integrity of the aging antigenic site; (b) COOH (residues 812–827) is part of senescent cell antigen and an anion binding site; (c) ANION 1 (538–554), which has been reported to be a transport segment of band 3, does not bind sulfate; and (d) lysines contribute to anion binding but are not the only amino acid(s) required for anion binding and, thus, anion transport. cl Materials and Methods Cell Separation. Red blood cells were separated into populations of different ages on Percoll gradients as previously described (3). Middle-aged cells were stored in Alsever's for 5 wks at 4° C.

Purification of senescent cell IgG (SCIgG) for analysis. IgG was isolated from senescent RBC from 50 liters of blood as previously described (2, 4, 7, 29). IgG eluted from senescent cells, rather than serum IgG, was used because normal serum contains antibodies to spectrin, actin, 2.1, etc. (6). RBC were washed three times with 50–100 volumes of Dulbecco's phosphate buffered saline (PBS), pH 7.4. IgG was eluted from RBC membranes (ghosts) prepared by digitonin lysis, washed 3 times with PBS, and IgG eluted with 0.1M glycine-HCl buffer, pH 2.3 (2, 4, 7, 29). Eluates were neutralized with 1N NaOH, concentrated, and 0.02% NaDodSO$_4$ and 0.05% Tween 20 added. Samples were incubated with Protein A Sepharose 4B overnight, and the IgG was eluted with 2 vols. of glycine-HCl buffer, pH 2.3, after extensive high salt/low salt washes. Eluted IgG was neutralized with 1 N NaOH, and dialyzed against PBS.

IgG binding and inhibition assay. Competitive inhibition studies were performed using synthetic peptides to absorb the IgG isolated from senescent erythrocytes. This is the same IgG that initiates phagocytosis in situ. The Fc portion IgG is required for binding and phagocytosis of cells by macrophages (3, 2, 4, 7, 29). Fab fragments were not used because we were simulating the physiological situation. Intact dimeric, senescent cell IgG containing the Fc portion binds to senescent cells in situ and initiates their removal (3, 32, 2, 4, 6, 17, 7). Only IgG isolated from aged erythrocytes binds specifically to senescent cells. For example, IgG eluted from young control erythrocytes did not bind to senescent cells (2, 4, 6, 17, 7). Moreover, the specific binding capacity of the autoantibody was eliminated by absorption with purified senescent cell antigen (39). SCIgG (3 ug) was absorbed with synthetic peptides at the concentrations indicated or purified SCA, as a control, for 60 min at room temperature, and incubated with stored red cells for 60 min at room temperature (2, 4, 6, 17, 7). Storage mimics normal aging in situ immunologically and biochemically (32, 2, 4, 6, 29, 7). After incubation with absorbed IgG, cells were washed four times with 40–50 volumes of phosphate buffered saline containing 0.2% bovine serum albumin (BSA, fraction V, Sigma, St. Louis, Mo.) and 0.5% glucose. Washed cells were transferred to BSA-coated tubes ($5 \times 10^7$ cells/50 ul) and incubated for 30 min. at 37° C. with $^{125}$I-Protein A (Amersham, Arlington Heights, Ill. 30–38 mCi/mg, 10–15 ng/tube). Cells were then washed four times and transferred to new tubes before counting in a gamma scintillation counter (Beckman, Gamma 5,500). The number of red cell-bound IgG molecules was quantitated before and after absorption using equilibrium binding kinetics (7).

Scatchard analysis was performed. Scathard, *NY Acad. Sci.* 51:660–672 (1949), incorporated herein by reference. Percent inhibition was calculated from the following formula: 100[1-(x-b)/T-b)] where x=molecules of IgG autoantibody bound per cell; T=total number of IgG antibody molecules bound in the absence of inhibitor; b=background Protein A binding.

Peptides. Peptides were prepared by solid phase synthesis using an Applied Biosystems 430A automatic peptide synthesizer, analyzed for purity, and treated as previously described in Example 1. For the present studies, we used the two peptides which carry the aging antigenic determinants, ANION 1 and COOH. ANION 1 (538–554: SKLIKIFQDHPLQKTYN) is a putative transport peptide that includes two important amino acids. The lysine at 538 (558 in the mouse) is a covalent binding site for the anion transport inhibitor, diisothicyano dihydrostilbene disulphonate (DIDS), and the tyrosine at residue 553 is radio-iodinated by extracellular lactoperoxidase (34). COOH, a peptide from the carboxyl terminus region (COOH, 812-827: LFKPPKYHPDVPYVKR), contains both hydrophobic and hydrophylic regions. The lysines found in this region may comprise another binding site for DIDS (35). The second anion transport region peptide is situated toward the end of the region and is probably intracellular because the potential N-glycosylation site at ASN-593 is not glycosylated (44) (ANION 2, 588–602: LRKFKNSSYFPGKLR). This peptide is only slightly inhibitory as shown in Example 1. Peptides were synthesized based on the sequence data from the paper by Tanner et al. (34).

For dinitroflurobenzene (DNFB) modification, peptides were incubated with DNFB (Eastman Kodak) overnight in borate buffered saline at room temperature, and dialysed to remove DNFB according to standard procedures (43). Derivatization was determined by spectral absorption. Unmodified peptides absorb at 280 nm. DNP modified peptides absorb at 360 nm. Unmodified peptide and DNFB are colorless. As coupling occurs, the solution turns a brilliant yellow, and the coupled protein remains yellow. DIDS modification was performed in the same manner.

Anion transport and DIDS inhibition measurements. Sulfate exchange is inhibited by 4,4'-diisothiocyano-2,2' disulfonic acid. Stilbenedisulfonate derivatives such as DIDS inhibit anion transport by binding to at least two lysine residues in the membrane-spanning region of band 3 (45, 23, 35).

Peptide inhibition of sulfate "influx" experiments were performed essentially according to method of Jennings (46) using 300 mM sucrose, 10 mM Tris-HEPES, pH 7.0, as the "influx" buffer (47). Washed cells were incubated in 20–30 volumes of 110 mM $K_2SO_4$ for 10 min at 37° C. to replace intracellular chloride. The cells were centrifuged and the supernatant removed and replaced with 110 mM $K_2SO_4$ for 10 min. This was repeated 3 times. After the last centrifugation, cells were resuspended 300 mM sucrose, 10 mM Tris-HEPES, pH 7.0, and washed once. Cells were suspended to $2 \times 10^8$ cells/ml in 2 ml influx buffer at 37° C. Radioactive sulfate (0.01 mM) was added (582 mCi/mM) at suitable time intervals. Samples were taken and added to 18 volumes of ice cold 1.15% KCl (154 mM KCl) buffered to pH 7.4 with MOPS ("wash buffer"). The high chloride concentration, temperature, and pH all inhibit sulfate transport. Cells were washed twice to remove external sulfate at 0° C. with wash buffer. All samples were deproteinized with trichloracetic acid (final concentration 6.7%) and counted with Ready-Solv HP/6 (Beckman, Fullerton, Calif.) in a liquid scintillation counter. For peptide inhibition of sulfate transport, 0.01 mM of peptide(s) were added to the radioactive sulfate prior to addition to cells suspended in influx buffer.

Results and Discussion

Identification of lysine as an active amino acid in the aging antigenic site. In order to define the aging antigenic site along the band 3 molecule and to determine the active antigenic residues, we changed the lysines known to bind DIDS from these positively charged amino acids to acidic or neutral residues. This abolished antigenicity as determined by senescent IgG binding inhibition.

First, we modified the two active peptides, ANION 1 and COOH with dinitrofluorobenzene (DNFB), which substitutes a amino and e amino groups on a peptide or protein. In the case of ANION 1, the lysines in positions 2, 5, and 14, the tyrosine in position 16, and the serine at the amino terminus would all be modified by the addition of a DNP group. In the case of peptide COOH, the lysines at positions 3, 6, and 15, the tyrosines at 7 and 13, and the leucine at the amino terminus would be modified by the addition of DNP. The addition of DNP confers two negative charges where previously there had been a positively charged lysine or uncharged tyrosine. The addition of the DNP groups to ANION 1 and COOH abolished the ability of these peptides to inhibit IgG binding (Table 3). Thus, additions of DNP to a and e amino groups destroyed the antigenicity of synthetic senescent cell antigen, the synergistic mixture of ANION 1 and COOH. DNP modified ANION 1 or COOH alone resulted in IgG inhibition of 16% when it was mixed with its unmodified partner peptide.

Because DNFB modified a amino as well as e amino groups, we decided to use $H_2DIDS$ (4,4'-diisothiocyanodihydrostilbene-2,2'- disulfonate), which modifies only lysines, to modify our two active peptides.

DIDS is a specific, irreversible, inhibitor of anion transport. It binds covalently. Jennings et al. (35) presented evidence that one of the sites for the cross-linking of band 3 by extracellular H2DIDS is a lysine located between residues 814 and 829, although other scientists dispute this. The former is included in our peptide COOH. Another covalent attachment site for DIDS has been localized to lysine 539 using site directed mutagenesis (48). This lysine is on our peptide ANION 1. The addition of the DIDS groups to ANION 1 and COOH abolished the ability of these peptides to synergize in the inhibition of IgG binding (Table 4).

Figure 7:
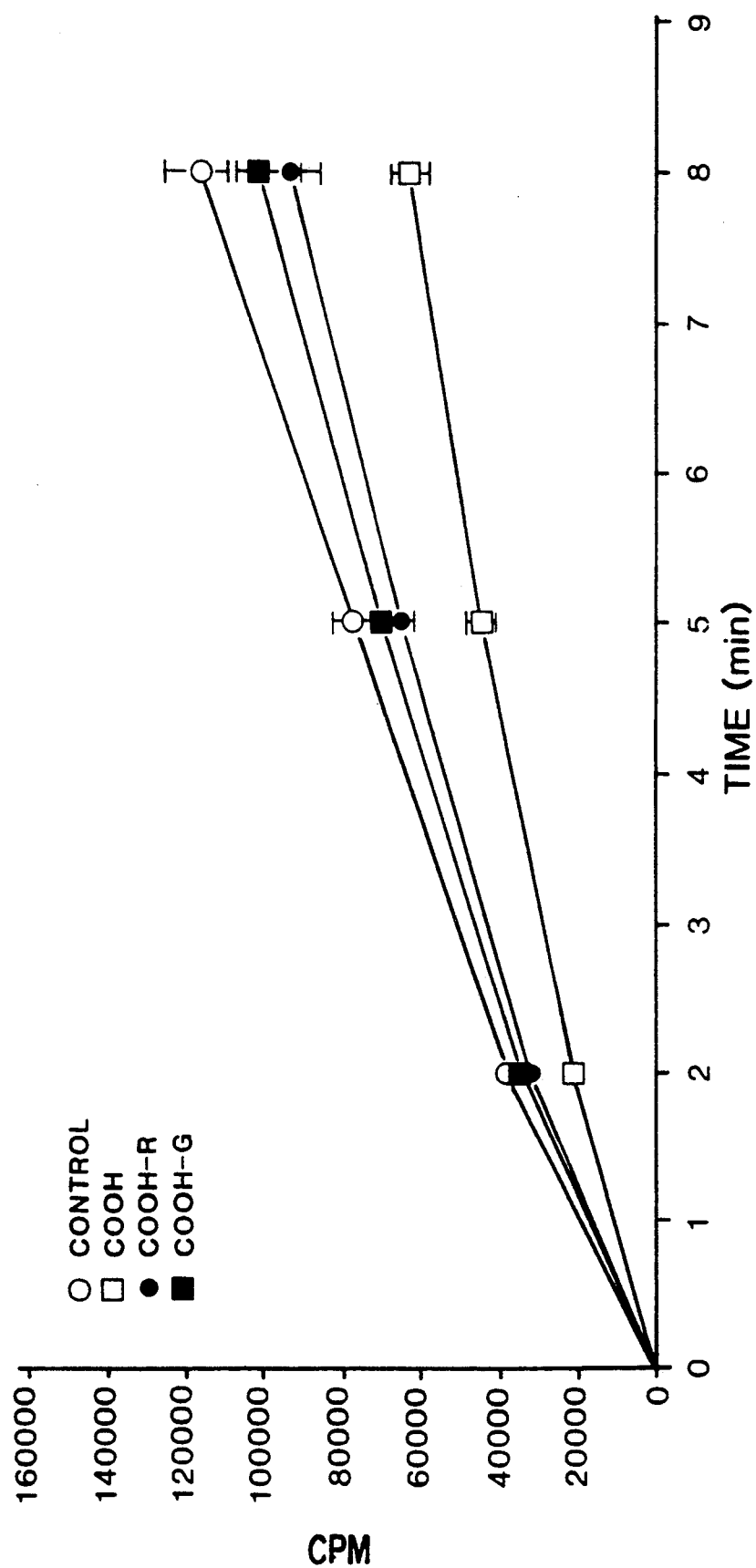

Thus, additions of DIDS to lysines destroyed the antigenicity of the synergistic mixture, ANION 1 and COOH. DIDS modified ANION 1 appeared to abolish its ability to synergize with COOH; whereas, DIDS modification of COOH appeared to destroy its antigenicity (Table 4). DIDS modified ANION 1 alone was relatively unaffected whereas DIDS modified COOH alone gave no IgG inhibition. Based on these results, it appears that (a) either the active antigenic amino acids on COOH include DIDS accessible lysines or that lysines are close enough to the active antigenic amino acids that steric perturbation caused by their modification alters the binding site; and (b) lysines on ANION 1 are probably required for synergism. Since an antibody binding site is 6 amino acids in size, it is likely that the antibody binding site of senescent cell IgG contains a lysine(s) contributed by COOH given the placement of the 3 lysines along each peptide. Certain lysines on ANION 1 could be blocked by hydrophobic amino acids such as isoleucine and thus not be accessible to DIDS. The results further suggest that COOH may contribute most of the antigenic determinants.

Abolition of the inhibition of senescent cell IgG caused by ANION 1 and COOH following DNP and DIDS modification of these peptides is further evidence for the specificity of their inhibition in the IgG binding assay. Thus, modified ANION 1 and COOH serve as a control for the unmodified peptide.

Since DNP and DIDS modification of ANION 1 and COOH abolished inhibition of senescent cell IgG binding, we reasoned that DIDS binding to band 3 lysines in whole cells should interfere with senescent cell IgG binding. Stored cells were incubated with 25 uM DIDS for 90 min at room temperature prior to incubation with senescent cell IgG. This resulted in 54±3% inhibition of binding. This data suggest that at least one lysine lies in or near the senescent cell autoantibody binding site. Another possibility is that DIDS binding perturbs the configuration of the molecule so that the binding site is altered. However, since our studies indicate that the actual antigenic determinants reside on ANION 1 and COOH (Example 1), it is unlikely that a distant perturbation of the antigenic site by DIDS binding is responsible. It is more likely that a DIDS reactive lysine lies in or near enough to the antigenic site to cause steric hindrance.

We then tried substituting a neutral or positively charged amino acid for the positively charged lysine in COOH peptide (LFKPPKYHPDVPYVKR). Substitution of either neutral glycines (COOH-G: LFGPPGYHPDVPYVGR) or positively charged arginines (COOH-R: LFRPPRYHPDVPYVRR) for lysine in COOH reduced its activity in the competitive inhibition assay with senescent cell IgG (FIG. 5). This suggests that (a) charge alone is not the critical determinant of antigenicity, and (b) lysines contribute to the antigenicity of the aging antigen. Since we changed all of the three lysines in the synthetic peptide COOH, we cannot determine at this time whether all lysines are critical or whether antigenicity depends on a specific lysine.

COOH is part of an anion binding site. Anion transport has been attributed to the general region of ANION 1 and COOH by some investigators based on indirect evidence (35, 46, 34). We suspected that senescent cell antigen is related to the anion transport site because peptide mapping studies and anion transport studies suggested that a cleavage of band 3 occurs in the anion transport region (5). Furthermore, breakdown products of band 3 are observed in the oldest cell fractions but not in young or middle-aged cell fractions (5), fragments of the cytoplasmic segment of band 3 are present in the cytoplasm of old red cells and of red cells with a band 3 alteration that results in accelerated aging (Example 1), anion transport is impaired in old cells (30, 6, 17), and band 3 mutations/alterations that result in damage to the transmembrane transport region result in increased IgG binding and accelerated aging (7, 17). Therefore, we performed inhibition studies with COOH and related peptides using equimolar amounts of peptide and sulfate (FIG. 6).

We focused on COOH because the DIDS modification studies of COOH and ANION 1 described earlier suggested that COOH contributes most of the antigenic determinants of the aging antigen. Furthermore, ANION 1 peptide does not inhibit anion transport in our assay system (8±7% inhibition). Results of studies using mouse band 3 expressed in Xenoous Laevis oocytes (49) indicates that lysine 558 in the mouse sequence (539 on ANION 1 in the human sequence) is not involved in anion transport although it is involved in DIDS binding (48). There are two other lysines on ANION 1. However, our studies show that ANION 1 does not inhibit anion transport (8±7% inhibition in our assay). Thus, the other two lysines on ANION 1 do not function as anion binding sites. Since ANION 1 does not inhibit anion transport even though it has 3 lysines, the anion transport binding must involve more than a mere positive charge. The configuration of the peptide is probably important. Our results agree with those of Bartel et al. (48) and Garcia and Lodish (50) based on site directed mutagenesis. Their studies show that the lysine at position 539 in the human and 558 in the mouse sequence is not involved in anion transport. Our studies show that synthetic peptide ANION 1 containing lysine 539 and two other lysines does not inhibit anion binding.

Residues 812–827 (COOH) and 813–818 (N6, the 6 amino acids on the amino side of COOH) are inhibitors of anion transport suggesting that these regions may be transport regions in situ. The mixture of COOH and ANION 1 also inhibits anion transport. COOH (residues 812–827) is part of senescent cell antigen and an anion binding site.

Residue 813–818 (N6, the 6 amino acids on the amino side of COOH) is both an inhibitor of anion transport and of senescent cell IgG binding (IgG binding inhibition: 48±1% at 10 ug) even though it is only six amino acids long. However, N6 (FKPPKY) does contain a proline-proline bend which may contribute to an anion pocket. It probably forms a loop in the membrane. These experiments suggest that at least part of the transport site is located on the same region of band 3 that generates senescent cell antigen.

In order to determine whether lysine was required for anion binding, we tested the COOH peptides which have an arginine or a glycine substituted for lysine. COOH resulted in 52±3% inhibition of anion transport at 5 min ($P \leq 0.001$ compared to control without peptide; see FIG. 7). Substitution of arginine residues for lysine resulted in inhibition of anion transport equal to that of COOH (46±4% inhibition; $P \leq 0.001$ compared to control without peptide). Substitution of glycines for lysines resulted in 27±6% inhibition ($P \leq 0.01$ compared to control without peptide). Thus, replacement of lysines with glycines or arginines reduces but does not abolish anion binding by the COOH peptide. The data suggest that lysine contributes to but may not be required for anion binding, and that other amino acids present in COOH peptide are probably involved in anion binding/transport (e.g. histidine, glutamine, arginine). The finding that DNP conjugation of ANION 2 does not alter its ability to inhibit transport supports this (inhibition: ANION 2, 38±4%, DNP-ANION 2, 39±5%; $P \leq 0.01$ for the difference between the two).

Figure 6:
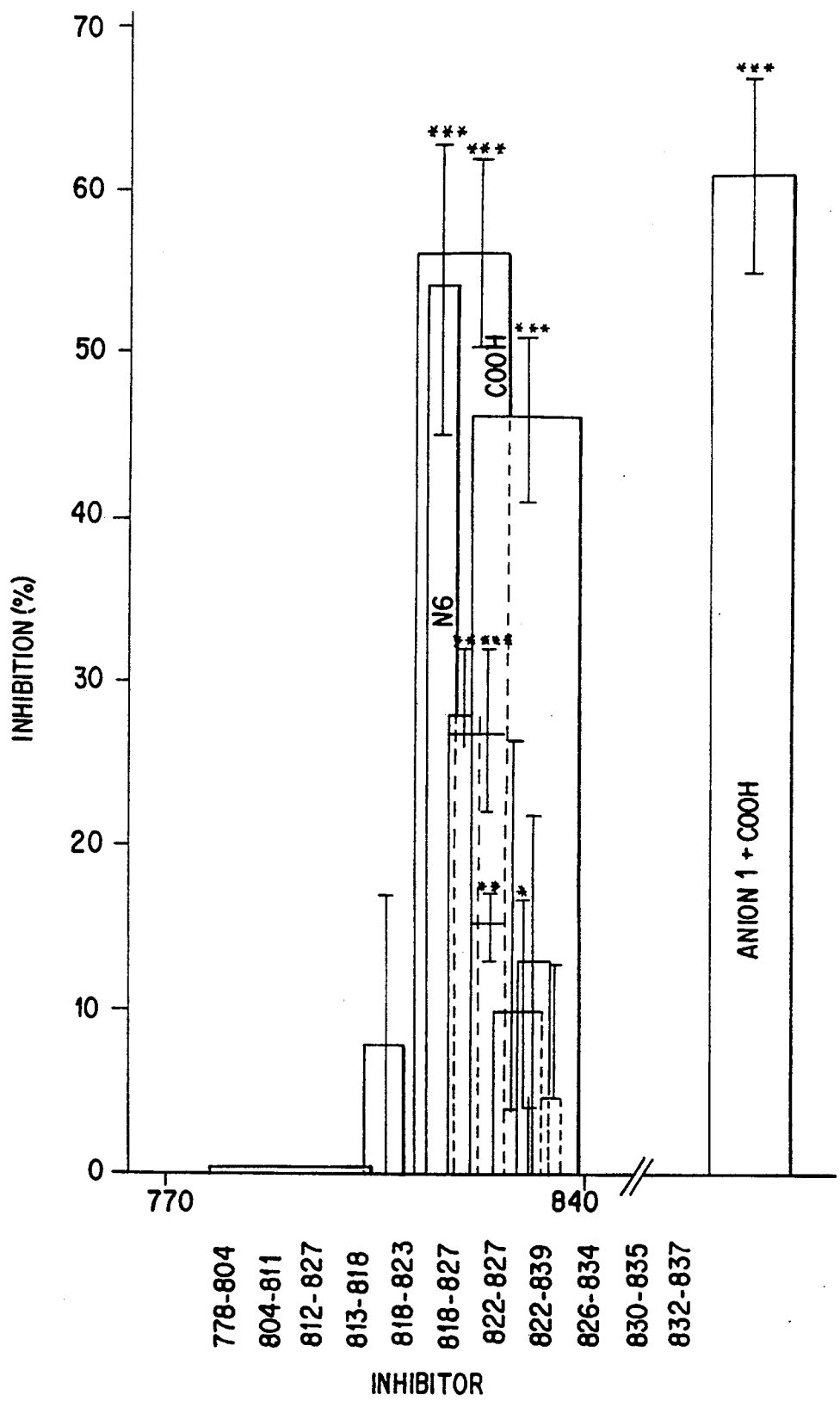

Investigators have suggested that lysines are not themselves part of the transport mechanism, but are close to the transport site, and that arginine is required for anion transport (24, 26). COOH-G has one arginine in it. Histidine and glutamine have also been implicated in anion transport (51, 52, 53). Our data suggest that several amino acids are involved in anion binding/transport and that an arginine may be one of them. The three dimensional structure of a transport site is more important than the actual amino acids. Many combinations of amino acids can probably generate a three dimensionally similar site. Furthermore, we specifically looked at the relationship between anion transport and senescent cell antigen. Thus, in this study, we did not "walk" the band 3 molecule in an attempt to identify all of the anion binding/transport sites. There are other segments of band 3 involved in anion transport toward the carboxyl terminus including residues 822–837 (FIG. 6). However, the data presented here indicate that ANION 1 is not involved in anion binding/transport and that COOH is involved.

Our data suggest that band 3 peptide COOH carries aging antigenic sites and is involved in anion transport, although it is not the only band 3 segment involved in anion transport. Results of this study indicate that: (a) lysines are required for the integrity of the aging antigenic site; (b) a DIDS reactive site lies in or near the antigenic site in intact red cells; (c) COOH (residues 812–827) is part of senescent cell antigen and an anion binding site with residues 813–818 being the most active; (d) ANION 1 (538–554), which has been reported to be a transport segment of band 3, does not bind anions; and (e) lysines themselves are not required for anion binding and, thus, for anion transport. Arginines can substitute for lysines without changing anion binding in the COOH peptide. Residues 812–827 (COOH) and 813–818 (N6, the 6 amino acids on the amino side of COOH) are inhibitors of anion transport when used in equimolar amounts with sulfate suggesting that these regions may be transport regions in situ. We suspect that the three dimensional structure of band 3 is a ring in which the two external loops on which ANION 1 and COOH reside are in close special proximity, forming senescent cell antigen as cells age. We do not expect a linear sequence of amino acids to be as effective as the three dimensional configuration in the band 3 molecule, nor do we expect short 6–8 mer peptides to be as effective inhibitors as longer ones.

TABLE 3

INHIBITION OF SENESCENT CELL IgG BINDING TO ERYTHROCYTES BY THE SYNTHETIC PEPTIDE MIXTURE OF ANION 1 AND COOH BEFORE OR AFTER DNP MODIFICATION[1]

| SYNTHETIC PEPTIDE MIXTURE | INHIBITION (%) |
|---|---|
| ANION 1 + COOH MX | 95 ± 1 |
| DNP-ANION 1 ± DNP-COOH MX | 0 |
| DNP-ANION 1 + COOH MX | 16 ± 1 |
| ANION 1 ± DNP-COOH MX | 16 ± 1 |

[1]Mx. mixture. Data are presented as the percentage inhibition ± standard deviation of triplicate or quadruplicate samples. Thirty ug of peptide mixture was used to test inhibition of binding of human autoantibody to senescent cell antigen on stored red cells.

TABLE 4

INHIBITION OF SENESCENT CELL IgG BINDING TO ERYTHROCYTES BY THE SYNTHETIC PEPTIDES OF BAND 3 PROTEIN BEFORE OR AFTER DIDS MODIFICATION

| SYNTHETIC PEPTIDE MIXTURE | INHIBITION (%) |
|---|---|
| ANION 1 + COOH MX | 95 ± 1 |
| DIDS-ANION 1 ± DIDS-COOH MX | 0 |
| DIDS-ANION 1 + COOH MX | 25 ± 7 |
| ANION 1 ± DIDS-COOH M | 12 ± 3 |
| DIDS-ANION 1 | 34 ± 3 |
| DIDS-COOH | 0 |
| ANION 1 | 32 ± 2 |
| COOH | 20 ± 1 |

MX, mixture. Data are presented as the percentage inhibition ± standard deviation of triplicate or quadruplicate samples. Thirty ug of peptide mixture was used to test inhibition of binding of human autoantibody to senescent cell antigen on stored red cells. Unmodified ANION 1, and COOH results are from a separate experiment.

REFERENCES

1. Kay, M. M. B. (1975) Proc. Natl. Acad. Sci. 72, 3521–3525.
2. Kay, M. M. B. (1978) J. Supramol. Struct. 9, 555–567.
3. Bennett, G. D. & Kay, M. M. B. (1981) Exp. Hematol. 9, 297–307.
4. Kay, M. M. B. (1981) Nature 289, 491–494.
5. Kay, M. M. B. (1984) Proc. Natl. Acad. Sci. 81, 5753–5757.
6. Kay, M. M. B., Bosman, G. J. C. G. M., Shapiro, S. S., Bendich, A. & Bassel, P. S. (1986) Proc. Natl. Acad. Sci. USA 83, 2463–2467.
7. Kay, M. M. B., Flowers, N., Goodman, J. & Bosman, G. J. C. G. M. (1989) Proc. Natl. Acad. Sci. 86, 5834–5838.
8. Hebbel, R. P. & Miller, W. J. (1984) Blood 64, 733–741.
9. Singer, J. A., Jennings, L. K., Jackson, C., Doctker, M. E., Morrison, M. & Walker, W. S. (1986) Proc. Natl. Acad. Sci. USA 83, 5498–5501.
10. Glass, G. A., Gershon, H. & Gershon, D. (1983) Exp. Hematol. 11, 987–995.
11. Bartosz, G., Sosynski, M. & Wasilewski, A. (1982) Mech. Aging Dev. 20, 223–232.
12. Khansari, N. & Fudenberg, H. H. (1983) Cell. Immunol. 80, 426–430.
13. Kay, M. M. B., Goodman, S., Sorensen, K., Whitfield, C., Wong, P. Zaki, L. & Rudoloff, V. (1983) Proc. Natl. Acad. Sci. 80, 1631–1635.
14. Muller, H. & Lutz, H. U. (1983) Biochem. Biophys. Acta. 729, 249–257.
15. Friedman, M. J., Fukuda, M. & Laine, R. A. (1985) Science 228, 75–77.

16. Kay, M. M. B., Tracey, C. M., Goodman, J. R., Cone, J. C. & Bassel, P. S. (1983) Proc. Natl. Acad. Sci. 80, 6882-6886.
17. Kay, M. M. B., Bosman, G., Notter, M. & Coleman, P. (1988) Ann. N.Y. Acad. Sci. 521, 155-169.
18. Kellokumpu, S., Neff, L., Jamsa-Kellokumpu, S., Kopito, R. & Baron, R. (1988) Science 242, 1308-1311.
19. Schuster, V. L., Bonsib, S. M. & Jennings, M. L. (1986) Am J Physiol 251, C347-C355.
20. Hazen-Martin, D. J., Pasternack, G., Spicer, S. S. & Sens, D. A. (1986) J. Histochem. Cytochem. 34, 823-826.
21. Kudrycki, K. E. & Shull, G. E. (1989) J. Biol. Chem. 264, 8185-8192.
22. Lepke, S. & Passow, H. (1971) J. Membrane Biol. 6, 158-182.
23. Jennings, M. L. & Passow, H. (1979) Biochim. Biophys. Acta 554, 498-519.
24. Bjerrum, P. J., Wieth, J. O. & Minakami, S. (1983) J. Gen Physiol. 81, 453-484.
25. Steck, T. L. (1974) J. Cell Biol. 62, 1-19.
26. Bennett, V. (1979) Nature, Lond. 281, 597-599.
27. Kay, M. M. B. and Lin, F. (1990) Gerontology, in press.
28. Kay, M. M. B., Sorensen, K., Wong, P. & Bolton, P. (1982) Mol. Cell. Biochem. 49, 65-85.
29. Kay, M. M. B. (1988) in Methods in Hematology: Red Cell Membranes, eds. Shohet, S. & Mohandas, N. (Churchill Livingston, Inc., New York), pp. 135-170.
30. Bosman, G. & Kay, M. M. B. (1988) Blood Cells 14, 19-35.
31. Yam, P., Petz, L. D. & Spath, P. (1982) Am. Journal of Hematol. 12, 337-346.
32. Kay, M. M. B. (1975) Nature, 254, 424-426.
33. Devereux, J., Haeberli, P. & Smithies, O. (1984) Nucleic Acid Res. 12, 387-395.
34. Tanner, M. J. A., Martin, P. G. & High, S. (1988) Biochemical Journal 256, 703-712.
35. Jennings, M. L., Anderson, M. P. & Monaghan, R. (1986) J. Biol. Chem. 261, 9002-9010.
36. Zaki, L. (1983) Biochem. Biophys. Acta 110, 616-624.
37. Falke, J. J., Kanes, K. J. & Chan, S. I. (1985) J. Biol. Chem. 260, 13294-13303.
38. Kay, M. M. B., Lawrence, C., & Bosman, G. (1988) Proc. Natl. Acad. Sci. USA, 85, 492-496.
39. Kay, M. M. B., Lawrence, C., & Bosman, G. (1990) Brain Res. Bull. 24, 105-111.
40. Engelman, D. M., Steitz, T. A. & Goldman, A. (1986) Ann. Rev. Biophys. Com. 15, 321-353.
41. Kyte, J. & Doolittle, R. F. (1982) J. Mol. Biol. 157, 105-132.
42. Kay, M. M. B., Hughes, J., & Zagon, I. (1990) Proc. Heidelberg Acad. Sci.
43. Brock, C. J.; Tanner, M. J. A.; Kempf, C.: The human erythrocyte anion-transport protein. Biochem. J. 213: 577-586 (1983).
44. Williams, C. A.; Chase, M. W.: Methods in Immunology and Immunochemistry. Vol. 1:128-133 (1967).
45. Zaki, L.; Fasold, H.; Schumann, B.; Passow, H.: Chemical modification of membrane proteins in relation to inhibition of anion exchange in human red blood cells. J. Cell. Physiol. 86: 471-494 (1975).
46. Jennings, M. L.: Structure and function of the red blood cell anion transport protein. Annu. Rev. Biophys. Biophys. Chem. 18: 397-430 (1989).
47. Elgavish, A.; Smith, J. B.; Pillion, D. J.; Meezan, E.: Sulfate transport in human lung fibroblasts (IMR-90). J. Cell Physiol. 125: 243-250 (1985).
48. Bartel, D.; Hans, H.; Passow, H.: Identification by site directed mutagenesis of lysine 558 as a covalent attachment site of DIDS in mouse erythroid band 3. Biochem. Biophys. Acta 985: 355-358 (1989).
49. Morgan, M.; Hanke, P.; Grygorczyk, R.; Tintschl, A.; Fasold, H.; Passow, H.: Mediation of anion transport in oocytes of Xenopus Laevis by biosynthetically inserted band 3 protein from mouse spleen erythroid cells. EMBO J. 4: 1927-1931 (1985).
50. Garcia, A. M.; Lodish, H. F.: Lysine 539 of human band 3 is not essential for ion transport or inhibition of stilbene disulfonate. J. Biol. Chem. 264: 19607-19613 (1989).
51. Kawano, Y.; Okubo, K.; Tokunaga, F.; Miyata, T.; Iwanaga, S.; Hamasaki, N.: Localization of the pyridoxal phosphate binding site at the COOH-terminal region of erythrocyte band 3 protein. J. Biol. Chem. 263: 8232-8238 (1988).
52. Jennings, M. L.; Anderson, M. P.: Chemical modification and labeling of glutamate residues at the stilbenedisulfonate site of human red blood cell band 3 protein. J. Biol. Chem. 262: 1691-1697 (1987).
53. Jennings, M. L.: Evidence for an access channel leading to the outward-facing substrate site in human red blood cell band 3; in edited by Hamasaki, N.; Jennings, M. L.: Anion Transport Protein of the Red Blood cell Membrane. Proceedings of the International Meeting on Anion Transport Protein of the red blood cell membrane as well as kidney and diverse cells, Fukuoka, May, 1989, pp. 59-72 (Elsevier, N.Y. 1989).

We claim:

1. A peptide consisting essentially of a molecule of up to 40 amino acids linked by peptide bonds wherein said peptide is immunoreactive with antibodies to senescent cell antigen.

2. The peptide of claim 1 wherein said peptide is encoded by the nucleotide sequences 1612 to 1662 as shown in FIG. 1.

3. The peptide of claim 1 wherein said peptide is encoded by the nucleotide sequences 2434 to 2481 as shown in FIG. 1.

4. A peptide consisting essentially of the amino acid sequence SKLIKIFQDHPLQKTYN.

5. A peptide consisting essentially of the amino acid sequence LFKPPKYHPDVPYVKR.

6. A synthetic senescent cell antigen comprising a mixture of a first peptide encoded by the nucleotide sequences 1612 to 1662 as shown in FIG. 1 and a second peptide encoded by the nucleotide sequences 2434 to 2481 as shown in FIG. 1.

7. A synthetic senescent cell antigen comprising a mixture of a first peptide consisting essentially of the amino acid sequence SKLIKIFQDHPLQKTYN and a second peptide consisting essentially of the amino acid sequence LFKPPKYHPDVPYVKR.

8. The synthetic senescent cell antigen of claim 7 wherein said first and second peptides are covalently linked.

9. The synthetic senescent cell antigen of claim wherein each of said peptides is labeled with a detectable moiety.

10. The synthetic senescent cell antigen of claim 7 wherein each of said peptides is bound to an aqueous insoluble material.

11. The synthetic senescent cell antigen of claim 10 wherein said material is a membrane.

12. A pharmaceutical composition comprising a pharmaceutically effective amount of the peptide of claim 1 in a pharmaceutically acceptable carrier.

13. A pharmaceutical composition comprising a pharmaceutically effective amount of the synthetic senescent cell antigen of claim 7 in a pharmaceutically acceptable carrier.

14. The synthetic senescent cell antigen of claim 6 wherein said peptides are covalently linked.

15. The synthetic senescent cell antigen of claim 6 wherein each of said peptides is labeled with a detectable moiety.

16. The synthetic senescent cell antigen of claim 6 wherein each of said peptides is bound to an aqueous insoluble material.

17. The synthetic senescent cell antigen of claim 10 wherein said material is a membrane.

18. The peptide of claim 1 wherein said peptide is labeled with a detectable moiety.

19. The peptide of claim 4 wherein said peptide is labeled with a detectable moiety.

20. The peptide of claim 5 wherein said peptide is labeled with a detectable moiety.

21. The peptide of claim 1 wherein said peptide is bound to an aqueous insoluble material.

22. The peptide of claim 4 wherein said peptide is bound to an aqueous insoluble material.

23. The peptide of claim 5 wherein said peptide is bound to an aqueous insoluble material.

24. A pharmaceutical composition comprising a pharmaceutically effective amount of the peptide of claim 2 in a pharmaceutically acceptable carrier.

25. A pharmaceutical composition comprising a pharmaceutically effective amount of the peptide of claim 3 in a pharmaceutically acceptable carrier.

26. A pharmaceutical composition comprising a pharmaceutically effective amount of the peptide of claim 4 in a pharmaceutically acceptable carrier.

27. A pharmaceutical composition comprising a pharmaceutically effective amount of the peptide of claim 5 in a pharmaceutically acceptable carrier.

28. A pharmaceutical composition comprising a pharmaceutically effective amount of the synthetic senescent cell antigen of claim 6 in a pharmaceutically acceptable carrier.

29. A cosmetic composition comparing a cosmetically effective amount of the peptide of claim 1 in a cosmetically acceptable carrier.

30. A cosmetic composition comprising a cosmetically effective amount of the peptide of claim 2 in a cosmetically acceptable carrier.

31. A cosmetic composition comprising a cosmetically effective amount of the peptide of claim 3 in a cosmetically acceptable carrier.

32. A cosmetic composition comprising a cosmetically effective amount of the peptide of claim 4 in a cosmetically acceptable carrier.

33. A cosmetic composition comprising a cosmetically effective amount of the peptide of claim 5 in a cosmetically acceptable carrier.

34. A cosmetic composition comprising a cosmetically effective amount of the synthetic senescent cell antigen of claim 6 in a cosmetically acceptable carrier.

35. A cosmetic composition comprising a cosmetically effective amount of the synthetic senescent cell antigen of claim 7 in a cosmetically acceptable carrier.

36. The synthetic senescent cell antigen of claim 6 wherein the ratio of said first peptide to said second peptide is 40 to 60 by weight percent.

37. The synthetic senescent cell antigen of claim 7 wherein the ratio of said first peptide to said second peptide is 40 to 60 by weight percent.

* * * * *